United States Patent
Kiya et al.

(10) Patent No.: US 11,254,904 B2
(45) Date of Patent: Feb. 22, 2022

(54) CULTURE MATERIAL AND USE THEREOF

(71) Applicant: MITSUI CHEMICALS, INC., Tokyo (JP)

(72) Inventors: Makoto Kiya, Ichihara (JP); Hiroshi Miyasako, Chiba (JP); Katsutoshi Kinoshita, Chiba (JP); Tomoaki Matsugi, Kisarazu (JP); Takashi Oda, Ichihara (JP); Katsuhiro Esashika, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 17/279,036

(22) PCT Filed: Jun. 18, 2020

(86) PCT No.: PCT/JP2020/024020
§ 371 (c)(1),
(2) Date: Mar. 23, 2021

(87) PCT Pub. No.: WO2020/256079
PCT Pub. Date: Dec. 24, 2020

(65) Prior Publication Data
US 2021/0309954 A1    Oct. 7, 2021

(30) Foreign Application Priority Data

Jun. 21, 2019 (JP) .............................. JP2019-115392
Nov. 8, 2019 (JP) .............................. JP2019-203071

(51) Int. Cl.
*C12M 3/00* (2006.01)
*C12N 5/00* (2006.01)
(Continued)

(52) U.S. Cl.
CPC ........... *C12M 23/20* (2013.01); *C12N 5/0068* (2013.01); *C12M 1/22* (2013.01); *C12M 1/24* (2013.01);
(Continued)

(58) Field of Classification Search
CPC ..... C12M 23/20; C12M 25/14; C12N 5/0671; C12N 5/067
See application file for complete search history.

(56) References Cited

U.S. PATENT DOCUMENTS

2014/0322806 A1    10/2014 Bennett et al.
2021/0101176 A1*    4/2021 Baltazar .................. B05D 1/62

FOREIGN PATENT DOCUMENTS

JP    H01-112697 U    7/1989
JP    H08-149973 A    6/1996
(Continued)

OTHER PUBLICATIONS

English translation of JP 2009-292911, generated 2021.*
(Continued)

*Primary Examiner* — Nathan A Bowers
(74) *Attorney, Agent, or Firm* — Foley & Lardner LLP

(57) ABSTRACT

A culture material including a 4-methyl-1-pentene polymer for cells, tissues, or organs, the culture material having a water contact angle at a culture surface of 50° to 100°, a sagging distance by a test method described below of 0 to 5 mm, and an oxygen permeation rate at a temperature of 23° C. and a humidity of 0% of 4500 to 90000 $cm^3/(m^2 \times 24 \text{ h} \times atm)$. A test piece having the same material as the culture material and the same thickness as the culture surface of the culture material and having a flat plate shape of 100 mm long and 10 mm wide is made. The test piece is fixed onto a test board in a state where the test piece protrudes
(Continued)

lengthwise in a horizontal direction from a top surface of the test board, the top surface being horizontal.

14 Claims, 4 Drawing Sheets

(51) Int. Cl.
  *C12M 1/00* (2006.01)
  *C12N 5/071* (2010.01)
  *C12M 1/22* (2006.01)
  *C12M 1/24* (2006.01)

(52) U.S. Cl.
  CPC ............... *C12M 3/00* (2013.01); *C12N 5/067* (2013.01); *C12N 5/0671* (2013.01); *C12N 2533/30* (2013.01)

(56) References Cited

FOREIGN PATENT DOCUMENTS

| JP | H11-137241 A | 5/1999 |
|----|---|---|
| JP | 2001-190267 A | 7/2001 |
| JP | 2004-290111 A | 10/2004 |
| JP | 2009-292911 A | 12/2009 |
| JP | 2016-077164 A | 5/2016 |
| JP | 2016-520307 A | 7/2016 |

OTHER PUBLICATIONS

English translation of JP 2004-290111, generated 2021.*

Stevens, K. M., "Oxygen Requirements for Liver Cells in vitro," Nature, 1965, 206, p. 199.

Xiao et al., "The Importance of Physiological Oxygen Concentrations in the Sandwich Cultures of Rat Hepatocytes on Gas-Permeable Membranes," Biotechnol. Prog., vol. 30, No. 6, 2014, pp. 1401-1410.

Sakai et al., "Improving Oxygen Supply in Hepatocyte Culture", The Japanese Society for the Research of Hepatic Cells, searched on Apr. 9, 2019, http://hepato.umin.jp/kouryu/kouryu28.html (the attached is the same page retrieved on Mar. 3, 2021 and the machine translation by Google for the same page on Mar. 5, 2021).

* cited by examiner

CULTURE MATERIAL AND USE THEREOF

CROSS-REFERENCE TO RELATED APPLICATIONS

The present application claims priority under 37 U.S.C. § 371 to International Patent Application No. PCT/JP2020/024020, filed Jun. 18, 2020, which claims priority to and the benefit of Japanese Patent Application Nos. 2019-115392, filed on Jun. 21, 2019, and 2019-203071, filed on Nov. 8, 2019. The contents of these applications are hereby incorporated by reference in their entireties.

TECHNICAL FIELD

The present invention relates to a culture material and the use thereof.

BACKGROUND ART

Cells, tissues, and organs can be cultured only in conditions suitable for growth. Therefore, it is necessary to place cells, tissues, or organs in a culture vessel such as a dish, a plate, and a flask together with a medium (culture solution) containing appropriate nutrition, and then leave the culture vessel to stand in an incubator where temperature, humidity, and gas concentration can be kept at a certain level.

Further, sufficient and adequate oxygen is required to be supplied to efficiently achieve the culture described above.

Supplying gases such as oxygen and carbon dioxide in a culture vessel is necessary to supply oxygen to cells and carbon dioxide to a medium for pH adjustment. Therefore, a culture vessel made of a material such as glass and polystyrene, which have low gas permeability, is provided with an opening such as a cap and a lid at the top of the culture vessel to secure gas supply from the inside of an incubator to the inside of the vessel. However, most cultured cells generally adhere to the bottom surface or float in the vicinity of the bottom surface of the culture vessel, and the top surface is covered with a medium. Therefore, the oxygen diffusion rate in the medium is rate-limiting, leading to insufficient oxygen supply to the cultured cells particularly at the bottom portion and suppressed cell proliferation, which is a problem known for a long time. Further, polystyrene has autofluorescence and is hard to be observed with a microscope or the like, which is also a known problem (Non Patent Literature 1).

To facilitate oxygen supply to cells, there is means, for example, of increasing the partial pressure of oxygen in a culture apparatus. However, a dedicated culture apparatus is required that controls the partial pressure of oxygen, and the cost is generally high compared to a culture apparatus for culture under the atmosphere. In addition, an oxygen cylinder for use in controlling the partial pressure of oxygen contains a combustion-supporting gas, with the risk of oxidative heat generation, combustion, and explosion. Therefore, the oxygen cylinder should be carefully handled compared to a nitrogen cylinder and a carbon dioxide cylinder, each of which contains a non-flammable gas. It is known that, as an improved method for supplying oxygen in a convenient and practical manner, the use of a culture plate having a high oxygen-permeable film as a culture surface can simply solve the problem of oxygen diffusion rate limitation in a culture solution layer under static culture (Non Patent Literature 2).

For example, Sakai et al. from the University of Tokyo culture hepatocytes having a high oxygen consumption rate by using high oxygen-permeable polydimethylsiloxane (PDMS) at the bottom surface of a culture vessel. Consequently, such culture is reported to eliminate the oxygen deficiency state (anaerobic environment) seen in commercially available plates made of polystyrene, resulting in observation of the highly-self-organization phenomenon of hepatocytes (Non Patent Literature 3).

As high oxygen-permeable materials, in addition to the PDMS mentioned above, rubber materials such as polybutadiene (Patent Literature 1) have been studied. However, a gas-permeable film composed of a rubber material is likely to break due to low strength, and moreover, tends to warp when a medium is placed thereon and has an unstable shape. When warping occurs in a culture vessel, deformation of the vessel and damage resulting from the deformation cause cells that have attached to the inner wall of the culture vessel to fall away from the inner wall, and also cause cells during culture to gather at the warped portion, so that it is hard to culture cells efficiently. Since rubber materials are generally likely to cause adsorption and absorption of drug substances, the use of rubber materials in applications of drug discovery screening and diagnosis is restricted.

From the viewpoint of oxygen permeability, a non-polar polyethylene resin, polypropylene resin, or the like has been studied for use in a culture vessel. However, adjusting the thickness to have sufficient strength causes insufficient oxygen permeability, and such resins are opaque and hard to be observed with a microscope. Due to such problems, these resins are used only in some culture vessels such as a bag-shaped culture vessel. There is known a technology of disposing a support layer on the bottom surface of a culture vessel to keep the film thin and prevent the film from breaking and warping (Patent Literature 5). Unfortunately, the support layer hinders the view when cells are observed.

On the other hand, as a resin material that is superior in high oxygen permeability, a poly 4-methyl-1-pentene resin is exemplified. Patent Literatures 1 to 4 disclose a technology of a culture vessel comprising a film using a poly 4-methyl-1-pentene resin. Creative attempts are given to the film to enhance heat-sealing properties and flexibility, and the film can be suitably used as a culture vessel such as a horn-shaped or bag-shaped culture vessel for use in plant growth or floating cells. However, when applied for use in static culture, the film warps at the culture bottom surface and therefore is not appropriate as a culture vessel. In addition, the poly 4-methyl-1-pentene resin is, as it is, highly hydrophobic at the culture surface. Unfortunately, when the resin is used as a culture substrate, cells cannot attach to the substrate, fall away from the substrate, and die.

CITATION LIST

Patent Literatures

Patent Literature 1: JP 1-112697 Y
Patent Literature 2: JP 8-149973 A
Patent Literature 3: JP 11-137241 A
Patent Literature 4: JP 2001-190267 A
Patent Literature 5: JP 2016-077164 A

Non Patent Literatures

Non Patent Literature 1: Stevens, K. M., Oxygen requirements for liver cells in vitro., Nature, 206, 199 (1965)
Non Patent Literature 2: Xiao W, Shinohara M, Komori K, Sakai Y, Matsui H, Osada T, A (2014): The importance of physiological oxygen concentrations in the sandwich cultures of rat hepatocytes on gas-permeable membranes, Biotechnol. Prog., 30(6), 1401-1410

Non Patent Literature 3: Yasuyuki Sakai, "Enhanced oxygen supply in hepatocyte culture" [online] The Japanese Society for the Research of Hepatic Cells [searched on Apr. 9, 2019] Internet <http://hepato.uminjp/kouryu/kouryu28.html>

SUMMARY OF INVENTION

Technical Problem

The inventors of the present invention have considered that it is important to create a culture material that is superior in oxygen supply capacity with little deformation such as warping in order to culture cells, tissues, or organs (hereinafter, referred to as "cells, etc.") in vitro in a state closer to that in vivo. That is, the inventors of the present invention have considered that a culture vessel is required that has a stable shape, with the oxygen supply environment being strictly controlled, without relying solely on the oxygen concentration control by an incubator. Therefore, an object of the present invention is to provide a culture material and a culture vessel that are superior in shape stability and suitable for culture of cells, tissues, or organs where especially oxygen supply is required, emit no autofluorescence so as not to hinder observation of cells, and hardly sorb drugs. For culture of adherent cells, tissues, or organs, it is important to have shape stability and oxygen supply capacity as well as to keep adhesion of cells, etc. Therefore, a second object of the present invention is to provide a culture tool suitable for culture of adherent cells, tissues, or organs.

Solution to Problem

The present inventors have made intensive investigations to solve the above problems. Consequently, they have found that a culture material having the following configurations can solve the above problems, and completed the present invention. The present invention is, for example, the following items (1) to (14).

[1] A culture material including a 4-methyl-1-pentene polymer (X) for cells, tissues, or organs, the culture material having a water contact angle at a culture surface of 50° to 100°, a sagging distance by a test method (A) described below of 0 to 5 mm, and an oxygen permeation rate at a temperature of 23° C. and a humidity of 0% of 4500 to 90000 cm$^3$/(m$^2$×24 h×atm). Test method (A): A test piece having the same material as the culture material and the same thickness as the culture surface of the culture material and having a flat plate shape of 100 mm long and 10 mm wide is made. The test piece is fixed onto a test board in a state where the test piece protrudes lengthwise a length of 50 mm in a horizontal direction from a top surface of the test board, the top surface being horizontal. Three minutes after fixing, a measurement is performed of a distance of how much an end of the test piece protruding from the test board sags in a vertically downward direction from a horizontal plane including the top surface of the test board. (With the proviso that the process from the fixing to the measurement is performed at room temperature.)

[2] The culture material according to [1], wherein the 4-methyl-1-pentene polymer (X) is at least one type of polymer selected from a 4-methyl-1-pentene homopolymer (x1) and a copolymer (x2) of 4-methyl-1-pentene and at least one type of olefin selected from ethylene and an α-olefin having 3 to 20 carbon atoms (excluding 4-methyl-1-pentene).

[3] The culture material according to [1] or [2], wherein when a test method (B) described below is performed with rat primary-cultured liver cells to be seeded having a cell density of $1.0 \times 10^3$ cells/cm$^2$ to $4.0 \times 10^3$ cells/cm$^2$, a dissolved oxygen concentration in a culture solution after 1 hour is 2 to 20% of a saturated oxygen concentration in the culture solution for at least one point in the range of the cell density. Test method (B): A culture vessel including a cylindrical portion composed of polyethylene and a bottom surface portion having a flat plate shape and having the same material as the culture material and the same thickness as the culture surface of the culture material, the culture vessel having a culture area of 2 cm$^2$ and being coated with collagen, is made. The culture vessel is seeded with rat primary-cultured liver cells with 0.5 ml of a culture solution for rat primary-cultured liver cells and cultured at a temperature of 37° C., a carbon dioxide concentration of 5.0%, and an oxygen concentration of 20%. Twenty four hours after seeding, the culture solution is removed from the culture vessel, and 0.5 ml of the culture solution is newly added to the culture vessel. An oxygen concentration is measured at 80 μm height from a bottom surface of the culture vessel for 1 hour.

[4] The culture material according to [3], wherein when the test method (B) is performed with rat primary-cultured liver cells to be seeded having a cell density of $1.0 \times 10^5$ cells/cm$^2$ to $4.0 \times 10^3$ cells/cm$^2$, an oxygen consumption rate is 40 to 150 pmol/s/10$^5$ cells for at least one point in the range of the cell density.

[5] The culture material according to any one of [1] to [4], which is a film, a sheet, or a culture vessel.

[6] The culture material according to [5], wherein the culture vessel is a petri dish, a flask, an insert, a plate, a bottle, or a bag.

[7] The culture material according to any one of [1] to [6], wherein the culture surface is microfabricated.

[8] A microchannel device including the culture material according to [7].

[9] A culture vessel, wherein at least a culture surface is formed of the culture material according to any one of [1] to [7].

[10] The culture vessel according to [9], including at least one well.

[11] A culture tool including the culture material according to any one of [1] to [7] or the culture vessel according to [9] or [10].

[12] The culture tool according to [11], wherein the culture surface is coated with a natural polymer material, a synthetic polymer material, or an inorganic material.

[13] A method for culturing cells, tissues, or organs, including a step of incubating cells, tissues, or organs in the culture tool according to [11] or [12].

[14] The method for culturing cells, tissues, or organs according to [13], wherein the cells, tissues, or organs are liver cells.

Advantageous Effects of Invention

According to the present invention, provided are a culture material and a culture vessel that are superior in shape stability, can achieve a suitable oxygen environment for culture of cells, tissues, or organs, emit no autofluorescence so as not to hinder observation of cells, and hardly sorb drugs. Also, provided is a culture tool that keeps cell adhesion suitable for culture of adherent cells, tissues, or organs.

DESCRIPTION OF EMBODIMENTS

Figure 1:
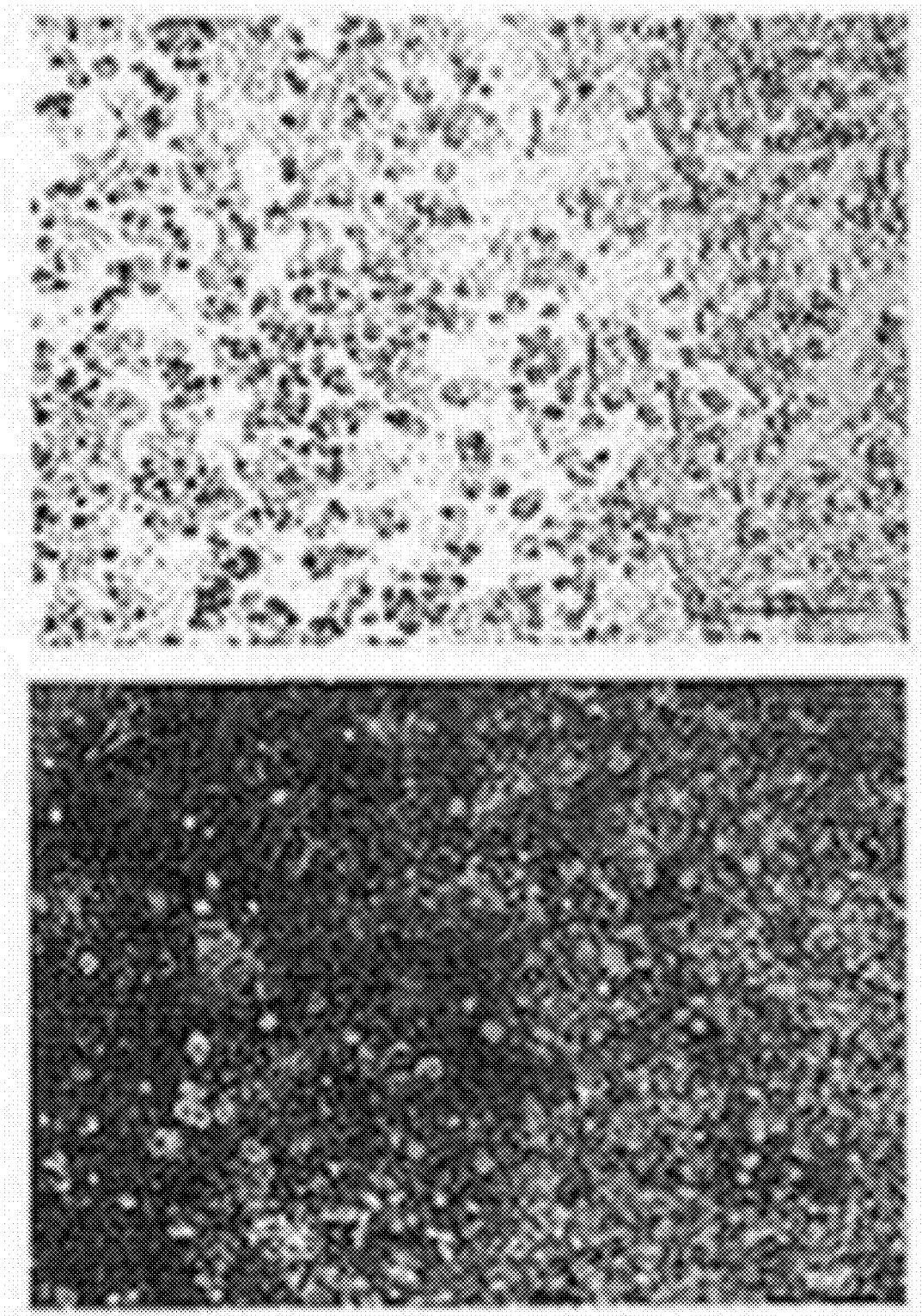
FIG. 1 shows photographs of cells of Example 1 observed with a phase-contrast microscope (upper: 1 day after, lower: 7 days after).

The present invention is broadly categorized into four aspects.

A first aspect of the present invention is a culture material including a 4-methyl-1-pentene polymer (X) for cells, tissues, or organs, the culture material having a water contact angle at a culture surface of 50° to 100°, a sagging distance by a test method (A) described below of 0 to 5 mm, and an oxygen permeation rate at a temperature of 23° C. and a humidity of 0% of 4500 to 90000 $cm^3/(m^2 \times 24 \, h \times atm)$. Test method (A): A test piece having the same material as the culture material and the same thickness as the culture surface of the culture material and having a flat plate shape of 100 mm long and 10 mm wide is made. The test piece is fixed onto a test board in a state where the test piece protrudes lengthwise a length of 50 mm in a horizontal direction from a top surface of the test board, the top surface being horizontal. Three minutes after fixing, a measurement is performed of a distance of how much an end of the test piece protruding from the test board sags in a vertically downward direction from a horizontal plane including the top surface of the test board. With the proviso that the process from the fixing to the measurement is performed at room temperature.

A second aspect of the present invention is a culture vessel in which at least a culture surface is formed of the culture material of the first aspect.

A third aspect of the present invention is a culture tool including the culture material of the first aspect or the culture vessel of the second aspect.

A fourth aspect of the present invention is a method for culturing cells, tissues, or organs including a step of incubating cells, tissues, or organs in the culture tool of the third aspect.

Hereinafter, specific embodiments of the present invention will be explained in detail. However, the present invention is not particularly limited to the following embodiments, and can be performed with modification as needed within a scope of the objects of the present invention.

The description with regard to the number range "A to B" indicates A or more and B or less unless otherwise noted. For example, the description of "1 to 5%" means 1% or more and 5% or less.

<4-methyl-1-pentene Polymer (X)>

The term "polymer" as used herein includes a homopolymer and a copolymer. In the same manner, the term "polymerization" as used herein includes homopolymerization and copolymerization. Therefore, "4-methyl-1-pentene polymer (X)" conceptually includes a homopolymer of 4-methyl-1-pentene and a copolymer of 4-methyl-1-pentene and other monomer. Hereinafter, a homopolymer of 4-methyl-1-pentene is also referred to as a "4-methyl-1-pentene homopolymer (x1)".

The copolymer of 4-methyl-1-pentene and other monomer may be any one of a random copolymer, an alternating copolymer, a block copolymer, and a graft copolymer. The copolymer of 4-methyl-1-pentene and other monomer may be preferably a copolymer (x2) of 4-methyl-1-pentene and at least one type of olefin selected from ethylene and an α-olefin having 3 to 20 carbon atoms (excluding 4-methyl-1-pentene) due to high strength (hardly breaks and splits) and little warping of the substrate.

The 4-methyl-1-pentene polymer (X) is preferably at least one type of polymer selected from a 4-methyl-1-pentene homopolymer (x1) and a copolymer (x2) of 4-methyl-1-pentene and at least one type of olefin selected from ethylene and an α-olefin having 3 to 20 carbon atoms (excluding 4-methyl-1-pentene), and more preferably a copolymer (x2) of 4-methyl-1-pentene and at least one type of olefin selected from ethylene and an α-olefin having 3 to 20 carbon atoms (excluding 4-methyl-1-pentene).

Examples of the olefin include ethylene, propylene, 1-butene, 1-hexene, 1-heptene, 1-octene, 1-decene, 1-tetradecene, 1-hexadecene, 1-heptadecene, 1-octadecene, and 1-eicosene. The olefin can be selected as appropriate depending on the necessary physical properties for the culture material. From the viewpoint of appropriate oxygen permeability and superior rigidity, the olefin may be preferably an α-olefin having 8 to 18 carbon atoms, and more preferably at least one type selected from 1-octene, 1-decene, 1-dodecene, 1-tetradecene, 1-hexadecene, 1-heptadecene, and 1-octadecene. When the number of carbon atoms in the olefin falls within the range described above, the polymer has better film formation processability. As a result, when the polymer is molded and released from a roll or a metal mold, poor appearance due to cracks or splits at edge portions tends to hardly occur. Therefore, the culture material has low incidence of poor products.

One type of olefin may be used, or two or more types of olefins may be used in combination. From the viewpoint of strength of the material, the number of carbon atoms is preferably 2 or more, and more preferably 10 or more. When different two or more types of α-olefins are used in combination, it is particularly preferable to combine at least one type selected from 1-tetradecene and 1-hexadecene and at least one type selected from 1-heptadecene and 1-octadecene.

The content of a structural unit derived from 4-methyl-1-pentene is preferably 60 to 100 mol %, and more preferably 80 to 98 mol %. The content of a structural unit derived from at least one type of olefin selected from ethylene and an α-olefin having 3 to 20 carbon atoms (excluding 4-methyl-1-pentene) is preferably 0 to 40 mol %, and more preferably 2 to 20 mol %. The contents of the structural units described above are given, with all repeating structural units being 100 mol %. When the contents of the structural units fall within the ranges described above, processability is superior, and a homogenous culture surface can be obtained. Further, a film has a good balance between toughness and strength, leading to less warping.

The 4-methyl-1-pentene polymer (X) may have a structural unit (hereinafter referred to as "other structural unit") other than the structural unit derived from 4-methyl-1-pentene and the structural unit derived from the olefin as long as the effect of the present invention is not impaired. The content of other structural unit is, for example, 0 to 10.0 mol %. When the 4-methyl-1-pentene polymer has other structural unit, the other structural unit may be of 1 type, 2 types, or more.

Examples of a monomer from which the other structural unit is derived include cyclic olefins, aromatic vinyl compounds, conjugated dienes, non-conjugated polyenes, functional vinyl compounds, hydroxyl group-containing olefins, and halogenated olefins. Examples of the cyclic olefins, aromatic vinyl compounds, conjugated dienes, non-conjugated polyenes, functional vinyl compounds, hydroxyl group-containing olefins, and halogenated olefins include compounds described in paragraphs [0035] to [0041] in JP 2013-169685 A.

The 4-methyl-1-pentene polymer (X) may be used singly, or two or more kinds of them may be used in combination. The culture material of the present invention need only contain the 4-methyl-1-pentene polymer (X), and may be formed only of the 4-methyl-1-pentene polymer (X) or formed of a composition containing the 4-methyl-1-pentene polymer (X).

The 4-methyl-1-pentene polymer (X) may be a commercially available product. Examples specifically include TPX MX001, MX002, MX004, MX0020, MX021, MX321, RT18, RT31, and DX845 (all trademarks) manufactured by Mitsui Chemicals, Inc. Any 4-methyl-1-pentene-based polymers that are manufactured by other manufacturers and meet the requirement above may be preferably used. The 4-methyl-1-pentene-based polymer (X) may be used singly, or two or more kinds of them may be used in combination.

When the culture material of the present invention is formed of a composition containing the 4-methyl-1-pentene polymer (X), the composition may contain a component other than the 4-methyl-1-pentene polymer (X), for example, a component described in the section of "additive" described later. When the culture material is formed of a composition containing the 4-methyl-1-pentene polymer (X), the content of the 4-methyl-1-pentene polymer (X) is preferably 90 to 100% by mass, more preferably 95 to 100% by mass, and particularly preferably 99 to 100% by mass, based on 100% by mass of the culture material. A large content of the component other than the 4-methyl-1-pentene polymer (X) not only lowers oxygen permeability but also lowers transparency and strength. The composition ratio of the 4-methyl-1-pentene polymer (X) specified in this range is taken at the culture surface of the culture material, and it may be different from this range at a portion with which cells are not directly in contact, such as a frame portion and a lid portion of the culture vessel.

The 4-methyl-1-pentene polymer (X) has a weight average molecular weight (Mw) measured by gel permeation chromatography (GPC) using standard polystyrene as a reference material of preferably 10000 to 2000000, more preferably 20000 to 1000000, and still more preferably 30000 to 500000. Here, the concentration of a sample at the time of GPC measurement may be, for example, 1.0 to 5.0 mg/ml. The 4-methyl-1-pentene polymer (X) has a molecular weight distribution (Mw/Mn) of preferably 1.0 to 30, more preferably 1.1 to 25, and still more preferably 1.1 to 20. A solvent used in GPC is not particularly limited as long as it dissolves the 4-methyl-1-pentene polymer (X), and orthodichlorobenzene is preferably used. An example of the measurement condition may be a condition shown in Examples described later, but the measurement condition is not limited thereto.

When the weight average molecular weight (Mw) is the upper limit described above or less, a film made by melt molding in a molding method for 4-methyl-1-pentene polymer (X) described later has a reduced occurrence of defects such as gel, leading to film formation with a uniform surface. Further, when a solution-cast method is employed, the solubility of the 4-methyl-1-pentene polymer (X) in a solvent is good, and a film has a reduced occurrence of defects such as gel, leading to film formation with a uniform surface.

When the weight average molecular weight (Mw) is the lower limit described above or more, a film composed of the 4-methyl-1-pentene polymer (X), which is a culture material, has sufficient strength in vessel production and cell culture of the present invention. Furthermore, when the molecular weight distribution falls within the range described above, a prepared film can have a reduced/eliminated stickiness on its surface and also have sufficient toughness, leading to a reduced occurrence of bending at the time of film molding and cracks at the time of cutting.

For the weight average molecular weight (Mw) and the molecular weight distribution (Mw/Mn) of the 4-methyl-1-pentene polymer (X), when two or more kinds of polymers are used as the 4-methyl-1-pentene polymer (X), each Mw and Mw/Mn of each polymer need only fall within the range described above.

<Method for Producing 4-methyl-1-pentene Polymer (X)>

A method for producing the 4-methyl-1-pentene polymer (X) may be any methods that can polymerize 4-methyl-1-pentene, olefin, and other structural unit. To control the molecular weight and the molecular weight distribution, a chain transfer agent, for example, hydrogen may be coexistent. An apparatus used for production is also not limited. The polymerization method may be any publicly known methods, such as a vapor phase method, a slurry method, a solution method, and a bulk method. Preferred are a slurry method and a solution method. Furthermore, the polymerization method may be a single-step polymerization method or a multi-step (e.g., two-step) polymerization method in which a plurality of polymers having different molecular weights are blended in a polymerization system. In either method of the single-step polymerization method or the multi-step polymerization method, when hydrogen is used as a chain transfer agent, it may be charged at one operation or charged dividedly, such as in the early, middle, and late periods of polymerization. The production may be performed at room temperature or heated as needed; however, from the viewpoint of polymerization efficiency, preferably it is performed at 20° C. to 80° C., and particularly preferably 40° C. to 60° C. A catalyst used for production is also not limited. From the viewpoint of polymerization efficiency, a solid titanium catalyst component (I) described in WO 2006/054613 A is preferably used.

<Additive>

When the culture material of the present invention is formed of a composition containing the 4-methyl-1-pentene polymer (X), the composition may contain a component other than the 4-methyl-1-pentene polymer (X). Examples of the component other than the 4-methyl-1-pentene polymer (X) include additives such as heat-resistant stabilizers, light-resistant stabilizers, processing aids, plasticizers, antioxidants, lubricants, defoamers, antiblocking agents, colorants, modifiers, antibacterial agents, antifungal agents, and antifogging agents.

The 4-methyl-1-pentene polymer (X) has usually a melting point of 200° C. to 240° C. and high heat resistance. The 4-methyl-1-pentene polymer (X) undergoes no hydrolysis and thus is superior in water resistance, boiling water resistance, and steam resistance. Therefore, the culture material such as a culture vessel containing the 4-methyl-1-pentene polymer (X) can be subjected to a high-pressure steam sterilization treatment. The 4-methyl-1-pentene polymer (X) is characterized by having high visible light transmittance (usually 90% or more) and emitting no autofluorescence. Therefore, a culture vessel containing the 4-methyl-1-pentene polymer (X) facilitates observation of cultured cells. Further, the 4-methyl-1-pentene polymer (X) is superior in chemical resistance against most chemicals and hardly absorbs drugs and therefore can be suitably used in applications of drug discovery screening and diagnosis. The 4-methyl-1-pentene polymer (X) can be heat-sealed, and easily provides not only thermal fusion with the same material but also thermal adhesion with other material. In addition, the 4-methyl-1-pentene polymer (X) can be thermally molded and thus easily molded into a vessel of any shapes, for example, by an imprinting method or an insert method.

Since the 4-methyl-1-pentene-1 polymer (X) has superior characteristics described above, a culture vessel composed of the culture material of the present invention and a cell vessel in which a culture surface is formed of the culture material of the present invention cause no adverse effect on culture, are superior in stability, light transparency, and molding processability, and can be subjected to a sterilization treatment. Therefore, the 4-methyl pentene-1 polymer (X) is excellent as a material of the culture vessel.

<Method for Producing Film of 4-Methyl-1-Pentene Polymer (X)>

A method for producing the culture material of the present invention is not particularly limited. An apparatus used for production is also not limited. A film containing the 4-methyl-1-pentene polymer (X) and, as needed, the component other than the 4-methyl-1-pentene polymer (X) may be formed and molded into a culture material of a desirable shape. A culture material of a desirable shape may be directly molded by injection molding, blow molding, or other methods.

Examples of a method for forming a film specifically include commonly used methods such as an inflation method and a T-die extrusion method. The production is usually performed while heated. When the T-die extrusion method is employed, the extrusion temperature is preferably 100° C. to 400° C., and particularly preferably 200° C. to 300° C. The roll temperature is preferably 45° C. to 75° C., and particularly preferably 55° C. to 65° C.

The film of the present invention may be produced by a solution-casting method in which the 4-methyl-1-pentene polymer (X) is dissolved in a solvent, fed on a resin or metal, slowly dried while subjected to leveling, and formed into a film. The solvent used is not particularly limited, and a hydrocarbon solvent such as cyclohexane, hexane, decane, and toluene may be used. In consideration of solubility and drying efficiency of the resin, two or more kinds of solvents may be blended together. The polymer solution may be applied by a method such as table coating, spin coating, dip coating, die coating, spray coating, bar coating, roll coating, and curtain flow coating, and then dried and peeled to be processed into a film.

In either case, from the viewpoint of mass-production, it is preferable that a film containing the 4-methyl-1-pentene polymer (X) and, as needed, the component other than the 4-methyl-1-pentene polymer (X) is formed and molded into a culture material of a desirable shape.

<Cells, Tissues, or Organs>

Cells, tissues, or organs as used herein are also simply referred to as "cells, etc."

The cells as used herein are not particularly limited, and may be, in the case of animal cells, floating cells or adherent cells, such as fibroblasts, mesenchymal stem cell, hematopoietic stem cells, neural stem cells, nerve cells, corneal epithelial cells, oral mucosal epithelial cells, retinal pigment epithelial cells, periodontal ligament stem cells, myofibroblasts, cardiac muscle cells, liver cells, splenic endocrine cells, skin keratinocytes, skin fibroblasts, subcutaneous fat progenitor cells, kidney cells, bottom root sheath cells, nasal mucosal epithelial cells, vascular endothelial progenitor cells, vascular endothelial cells, vascular smooth muscle cells, osteoblasts, chondrocytes, skeletal muscle cells, immortalized cells, cancer cells, keratinocytes, embryonic stem cells (ES cells), EBV-transformed B cells, and induced pluripotent stem cells (iPS cells). The cells may be any one of primary-cultured cells and subcultured established cell lines. Skin, kidney, liver, brain, nerve tissue, cardiac muscle tissue, skeletal muscle tissue, cancer stem cells, and the like are high in oxygen demand, and cells constituting those are also high in oxygen demand. Therefore, cells as used herein are preferably cells constituting skin, kidney, liver, brain, nerve tissue, cardiac muscle tissue or skeletal muscle tissue; or cancer stem cells. As the cells, tissues, or organs, preferred are liver cells, renal cells, cardiac muscle cells, nerve cells, or cancer stem cells, and more preferred are liver cells.

The tissue as used herein means one in which similar cells gather together and function in a similar way. The tissue is not particularly limited, and examples include epithelial tissue, connective tissue, muscle tissue, and nerve tissue. Due to high oxygen demand, the tissue is preferably hepatic lobule, cardiac muscle tissue, nerve tissue, or skeletal muscle tissue, and more preferably hepatic lobule.

The organ as used herein means one in which the tissues described above gather together and work together for a purpose. Examples of the organ include, but not particularly limited to, lung, heart, liver, kidney, spleen, pancreas, gallbladder, esophagus, stomach, skin, and brain. Due to high oxygen demand, the organ is preferably skin, kidney, liver, or brain, and more preferably liver.

The cells, etc. are preferably cells, since cells are suitable for culture in a culture tool. The cells, etc. as used herein are preferably aerobic, and more preferably do not contain those that are anaerobic. The derivation of the cells, etc. is not particularly limited, and may be animals, plants, fungi, protists, bacterium, or any other organisms, preferably animals and plants, more preferably animals, and particularly preferably mammals. The culture tool as used herein has suitable oxygen permeability and keeps cell adhesion. Therefore, the cells, etc. are preferably adherent, and more preferably adherent cells.

<Liver Cell>

The liver cells as used herein may be any cells in liver, including hepatocytes, and examples specifically include vascular endothelial cells, vascular smooth muscle cells, adipose cells, blood cells, liver mononuclear cells, hepatic macrophages (including Kupffer cells), hepatic stellate cells, intrahepatic bile duct epithelial cells, and gallbladder fibroblasts. The liver cells are a cell population that contains, for example, hepatocytes in an amount of 20% or more, 30% or more, 40% or more, or 50% or more.

The liver cells may be any one of primary-cultured cells and subcultured established cell lines, and preferably primary-cultured cells. The type of the subcultured established cell line is not particularly limited, and examples include SSP-25, RBE, HepG2, TGBC50TKB, HuH-6, HuH-7, ETK-1, Het-1A, PLC/PRF/5, Hep3B, SK-HEP-1, C3A, THLE-2, THLE-3, HepG2/2.2.1, SNU-398, SNU-449, SNU-182, SNU-475, SNU-387, SNU-423, FL62891, and DMS153.

The derivation of the liver cells may be any mammals. In particular, cells of humans, cattle, dogs, cats, pigs, miniature pigs, rabbits, hamsters, rats, or mice are preferable, and cells of humans, rats, mice, or cattle are more preferable.

The liver cells may be a cell population that contains other cell types other than the liver cells. For example, the liver cells are a cell population that contains liver cells in an amount of 20% or more, 30% or more, 40% or more, or 50% or more.

<Culture>

The culture as used herein refers to a broad meaning including not only proliferation and maintenance of cells, etc. but also processes of seeding, subculture, differentiation induction, and self-organization induction of cells, etc. A medium etc. used for culture are not limited, and any mediums according to the characteristics of cells, etc. may be selected.

<Culture of Cells>

The culture of cells may be two-dimensional culture (including a case where cells are spontaneously multi-layered) or three-dimensional culture. The culture material of the present invention is good in oxygen permeation rate for culture and thus can supply oxygen to cells sufficiently not only in two-dimensional culture but also in three-dimensional culture where cells are stacked three-dimensionally. Consequently, cells proliferate and differentiate, and the highly-self-organization phenomenon of cells is likely to occur.

The three-dimensional culture is to intentionally culture cells three-dimensionally. Any one of a scaffold type where cells are cultured in a scaffold material and a scaffold-free type where cells are cultured as aggregates (spheroids) in a floating state may be used, with the scaffold type being preferred. In the case of the scaffold type, the scaffold material is preferably Matrigel (trademark), collagen gel, laminin, alginate hydrogel, or vitrigel, since those can culture cells efficiently. The medium etc. used for culture are not limited. To culture cells efficiently, cells are preferably cultured in the presence of serum (for example, bovine serum).

When the culture material of the present invention is used for culture, in other words, when a culture method of the present invention is performed using a culture tool of the present invention described later, the cell culture density is preferably $0.1 \times 10^3$ cells/cm$^2$ to $10.0 \times 10^3$ cells/cm$^2$, more preferably $0.5 \times 10^3$ cells/cm$^2$ to $5.0 \times 10^3$ cells/cm$^2$, still more preferably $1.0 \times 10^3$ cells/cm$^2$ to $4.0 \times 10^3$ cells/cm$^2$, and particularly preferably $1.5 \times 10^3$ cells/cm$^2$ to $3.5 \times 10^3$ cells/cm$^2$.

The cell culture density falling within the range described above is preferable since it allows drug metabolism activity to increase to a higher level, compared to a case where the cell culture density is beyond the range.

The culture material of the present invention is high in oxygen permeation rate and therefore can be suitably cultured even in a case where the cell culture density is high. In general, the cell density of a living body is believed to be about $2.5 \times 10^3$ cells/cm$^2$. The culture material of the present invention enables culture with the cell culture density nearly equal to that of a living body, and therefore enables culture in vitro in a state closer to that in vivo, which is preferable.

<Culture Material>

The culture material of the present invention is a culture material including a 4-methyl-1-pentene polymer (X) for cells, tissues, or organs, the culture material having a water contact angle at a culture surface of 50° to 100°, a sagging distance by a test method (A) described below of 0 to 5 mm, and an oxygen permeation rate at a temperature of 23° C. and a humidity of 0% of 4500 to 90000 cm$^3$/(m$^2$×24 h×atm).

The culture material means a material that is used to culture cells, and constitutes a culture vessel itself or a part of a culture vessel. When the culture material of the present invention constitutes a part of a culture vessel, at least a culture surface is constituted of the culture material of the present invention. The culture material of the present invention is, for example, a film, a sheet, or a culture vessel. When the culture material is a film or a sheet, the film or the sheet can be used as a part of a culture vessel including a culture surface. As the culture vessel, publicly known culture vessels of various types may be used, and the shape and size are not particularly limited. Examples include a petri dish (also referred to as dish), a flask, an insert, a plate, a bottle, and a bag. The culture vessel is usually used in an apparatus such as an incubator, a mass-culture apparatus, and a prefusion culture apparatus. The culture vessel is preferably a vessel having a bottom surface as a culture surface in order to keep and retain a medium. In general, a culture vessel having a shape of recess portion(s) such as well(s) on the bottom surface is required to have a thick bottom surface in order to stabilize the complicated shape of the bottom surface, leading to insufficient oxygen supply to cells, etc. The use of the culture material of the present invention allows even a plate having well(s) such as 1 well, 6 wells, 12 wells, 24 wells, 48 wells. 96 wells, 384 wells, and 1536 wells to have a stable shape and sufficient oxygen supply to cells, etc.

The culture material of the present invention means a culture material in which the culture surface is not coated with a natural polymer material, a synthetic polymer material, or an inorganic material serving as a scaffold for cells, etc.

The culture surface as used herein means, at the time of culture of cells, etc., a surface on which a medium is formed, a surface on which cells, etc. are seeded, or a surface on which a medium is formed and cells, etc. are seeded. That is, the culture surface is a concept that includes a surface on which a medium is supposed to be formed and a surface on which cells, etc. are supposed to be seeded.

The oxygen permeation rate of the culture material of the present invention at a temperature of 23° C. and a humidity of 0% is 4500 to 90000 cm$^3$/(m$^2$×24 h×atm), preferably 4500 to 67500 cm$^3$/(m$^2$×24 h×atm), more preferably 4500 to 47000 cm$^3$/(m$^2$×24 h×atm), and still more preferably 4500 to 45000 cm$^3$/(m$^2$×24 h×atm).

When the oxygen permeation rate of the culture material is too low, the oxygen concentration becomes low in the medium, leading to insufficient cell proliferation. On the other hand, when the oxygen permeation rate is too high, the oxygen concentration becomes too high in the medium, leading to reduced cell functions due to oxygen stress.

When the oxygen permeation rate falls within the range between the upper limit and the lower limit described above, cells have good firm attachment and keep good morphology and can efficiently proliferate depending on the culture period.

The thickness of the culture material when the culture material of the present invention is placed on a vessel bottom surface to prepare a culture vessel such as a petri dish, a flask, an insert, and a plate is not particularly limited, and is preferably 20 µm to 400 µm, more preferably 20 µm to 300 µm, and still more preferably 20 µm to 200 µm.

The thickness of the culture material is appropriately chosen depending on the form of the culture vessel. Adjusting the thickness falling within the range between the upper limit and the lower limit described above provides an appropriate oxygen concentration in the medium, which is necessary for cells to proliferate, and allows a suitable culture vessel to be prepared without warping (defined as a sagging distance) at the bottom surface of the culture vessel.

As an example of the culture vessel, a multi-well plate will be explained. In general, cell culture well plates in which the number of holes (referred also as wells) is 1, 6, 12, 24, 48, 96, 128, 384, and 1536 are commercially available. These vessels have the same size as a whole (the lengths of long side and short side), and the number of wells is defined by the diameter of holes. That is, a vessel having a large number of holes has a small hole diameter, while a vessel having a small number of holes has a large hole diameter. The large or small size of the diameter affects the warping of the culture material by stress resulting from the weight of the medium in a state where the culture material is directly placed on the bottom surface of the vessel and the medium is charged thereon. In general, a relatively thin culture material may be used in a vessel having a large number of holes (the diameter of holes is small), while a relatively thick culture material needs to be used in a vessel having a small number of holes (the diameter of holes is large).

The thickness of the culture material of the present invention is not particularly limited. Also, the thickness of the culture surface of the culture material of the present invention is not particularly limited, and preferably 20 to 500 µm, more preferably 25 to 500 µm, and particularly preferably 50 to 200 µm.

When the thickness of the culture material falls within the range described above, the culture material is superior in strength and thus preferable. In particular, when the thickness of the culture surface falls within the range described above, warping is less likely to occur even when the culture material is used in a vessel having a small number of wells and a large hole diameter. Further, the culture material is less likely to break when subjected to a corona treatment or the like. When the thickness of the culture surface falls within the range described above, the oxygen permeation rate falls within the range particularly suitable to culture cells, etc. that are high in oxygen demand.

The culture material of the present invention may be subjected to microfabrication on its surface in order to make spheroids and improve the scaffold function for cells. Since the 4-methyl-1-pentene polymer (X) is a type of thermoplastic resin, a method for microfabrication may be appropriately selected from methods such as cutting processing, optical lithography, electron beam direct drawing, particle beam processing, and scanning probe processing, and self-organization of fine particles; and molding processing methods using a master formed by these methods, represented by nanoimprinting, casting, and injection molding; and plating. The shape of microfabrication is not particularly limited, and the height from the bottom portion to the top portion of a trench is preferably 20 nm to 500 µm. The thickness of the thinnest portion may be reduced as thin as about 20 µm to hold sufficient strength, compared to the case of no microfabrication made on the surface.

The culture material that has been subjected to microfabrication may be used as a microchannel device (also referred to as microchannel chip). The microchannel device collectively represents devices in which microfabrication is performed on the surface of the culture material to make a microchannel or a reaction vessel, to be applied to bioresearch and chemical engineering. Examples include an apparatus called microTAS (micro Total Analysis Systems) or Lab on a Chip, and such an apparatus is aimed for use as a next-generation culture apparatus. As an aspect of the present invention, a microchannel device including the culture material of the present invention is exemplified.

The culture material of the present invention is preferably subjected to a hydrophilic treatment on its surface, in order to allow cells to firmly attach to the surface of the culture material suitably or, according to the purpose, to charge collagen or the like, which serves as a scaffold material during culture of cells, on the surface of the culture material to allow cells to firmly attach thereon. The surface free energy of the surface of the culture material can be defined by a water contact angle described later, and the water contact angle of the culture surface of the culture material is preferably 50° to 100°, more preferably 55° to 100°, and still more preferably 60° to 100°. As another preferred aspect of the water contact angle, 84° or less is exemplified, and 50° to 84° is more preferred.

Adjusting the water contact angle of the culture surface (surface) of the culture material of the present invention within the range described above allows, for example, liver cells to have good firm attachment to the culture material and uniformly proliferate on the surface of the culture material. The culture material in the form of having been subjected to a collagen treatment at the time of charging collagen can be used for cell culture, with collagen being uniformly charged on the surface of the culture material, being not peeled from the surface by washing with physiological saline solution or in the environment of cell culture, and keeping the stable initial state.

A method used for subjecting the surface of the culture material of the present invention to a hydrophilic treatment is not particularly limited, and examples include a corona treatment; a plasma treatment; an ozone treatment; an ultraviolet treatment; chemical vapor deposition; etching; addition of particular functional groups such as hydroxy, amino, sulfone, thiol, and carboxyl; treatments with particular functional groups such as silane coupling; and surface roughening with an oxidizing agent or the like. Among them, to increase wettability on the surface of the culture material and allow cells to be cultured efficiently on the surface, a surface hydrophilic treatment such as an ultraviolet treatment, a corona treatment, a plasma treatment, and an ozone treatment is preferably performed. These surface modification treatments may be performed singly, or two or more of them may be performed in combination. When a surface modification treatment is performed, it is preferably performed at least on the culture surface. When a plasma treatment is performed, as an accompanying gas, nitrogen, hydrogen, helium, oxygen, argon, or the like is used, and preferably at least one gas selected from nitrogen, helium, and argon is selected.

The culture material of the present invention is preferably a culture material for cells, and more preferably a culture material for liver cells.

<Measurement of Sagging Distance by Test Method (A)>

The culture material of the present invention has a sagging distance by a test method (A) of 0 to 5 mm, and preferably 0 to 3 mm. The test method (A) is as described below.

Test method (A): A test piece having the same material as the culture material and the same thickness as the culture surface of the culture material and having a flat plate shape of 100 mm long and 10 mm wide is made.

The test piece is fixed onto a test board in a state where the test piece protrudes lengthwise a length of 50 mm in a horizontal direction from a top surface of the test board, the top surface being horizontal.

Three minutes after fixing, a measurement is performed of a distance of how much an end of the test piece protruding from the test board sags in a vertically downward direction from a horizontal plane including the top surface of the test board. With the proviso that the process from the fixing to the measurement is performed at room temperature. The room temperature as used herein means 20 to 25° C.

The distance the test piece sags (mm) is designated as a sagging distance (mm). The sagging distance is an index of bending rigidity. That is, the shorter the sagging distance, the superior the bending rigidity of the culture surface of the culture material of the present invention.

A method for making a test piece is not particularly limited. For example, a test piece may be made by thermal molding such as extrusion molding a material that is the same as the culture material to make a test piece having a flat plate shape and then cutting out a test piece having the dimension described above from the sheet, or may be directly molded. When the culture material is a film or a sheet, a test piece may be cut out from the film or the sheet. Thermal molding in making a test piece is preferably performed in the same temperature condition (temperature and time) as that in producing a culture material. The test piece may be a test piece in which the culture material has been subjected to microfabrication and/or a surface modification treatment or has not been subjected to microfabrication and a surface modification treatment. Preferred is a test piece in which the culture material has not been subjected to any treatments.

When the sagging distance is more than 5 mm, the shape stability is insufficient. Specifically, warping occurs in the culture material, and deformation of the culture material and damage resulting from the deformation cause cells that have attached to the inner wall of the culture vessel to fall away from the inner wall and also cause cells during culture to gather at the warped portion, which makes it hard to culture cells efficiently.

<Oxygen Permeation Rate>

The culture material of the present invention has an oxygen permeation rate at a temperature of 23° C. and a humidity of 0% of 4500 to 90000 $cm^3/(m^2 \times 24\ h \times atm)$. For the culture material or a measurement sample made by using the same material as the culture material, the oxygen permeation rate $[cm^3 \times mm/(m^2 \times 24\ h \times atm)]$ at a temperature of 23° C. and a humidity of 0% is measured by a differential pressure gas permeability measuring method. Then, the value obtained by dividing the oxygen permeation rate by the thickness (μm) of the culture material is taken as an oxygen permeation coefficient. An apparatus used for measurement is not particularly limited, as long as it uses a differential pressure gas permeability measuring method. Examples include a differential pressure gas permeability measuring apparatus MT-C3 manufactured by Toyo Seiki Seisaku-Sho, Ltd. The measurement sample may be made by cutting out a test piece of 90×90 mm from a film of 50 μm thickness. The diameter of a measurement portion is preferably 70 mm (the permeation area is 38.46 $cm^2$). Due to high oxygen permeation rate, the sample is preferably masked with aluminum foil in advance to have an actual permeation area of 5.0 $cm^2$. The culture material or the measurement sample made by using the same material as the culture material, which are for use in measurement of oxygen permeation rate, may have been subjected to microfabrication and/or a surface modification treatment or not have been subjected to microfabrication and a surface modification treatment. Preferred is the culture material or the measurement sample that has not been subjected to any treatments.

<Dissolved Oxygen Concentration in Culture Solution by Test Method (B)>

For the culture material of the present invention, provided that a saturated oxygen concentration in a culture solution is 100%, when a test method (B) described below is performed with rat primary-cultured liver cells to be seeded having a cell density of $1.0 \times 10^3$ cells/$cm^2$ to $4.0 \times 10^5$ cells/$cm^2$, a dissolved oxygen concentration in a culture solution after 1 hour is preferably 2 to 20% of a saturated oxygen concentration in the culture solution for at least one point in the range of the cell density, more preferably 5 to 18%, still more preferably 5 to 16%, and most preferably 9 to 16%. A method for measuring the saturated oxygen concentration in the culture solution is not particularly limited, and examples include a measuring method using a fluorescence oxygen sensor (FireSting oxygen monitor, manufactured by BAS Inc.). The test method (B) is as described below.

Test method (B): A culture vessel including a cylindrical portion composed of polyethylene and a bottom surface portion having a flat plate shape and having the same material as the culture material and the same thickness as the culture surface of the culture material, the culture vessel having a culture area of 2 $cm^2$ and being coated with collagen, is made. The culture vessel is seeded with rat primary-cultured liver cells with 0.5 ml of a culture solution for rat primary-cultured liver cells and cultured at a temperature of 37° C., a carbon dioxide concentration of 5.0%, and an oxygen concentration of 20%. Twenty four hours after seeding, the culture solution is removed from the culture vessel, and 0.5 ml of the culture solution is newly added to the culture vessel. An oxygen concentration is measured at 80 μm height from a bottom surface of the culture vessel for 1 hour. The dissolved oxygen concentration falling within the range described above is preferable since the oxygen environment is in an optimal state for liver cells.

Measuring the oxygen concentration can be performed using a FireSting oxygen monitor (manufactured by BAS Inc.) or the like. When a FireSting oxygen monitor (manufactured by BAS Inc.) is used, a sensor is placed at 80 μm height from a bottom surface of the culture vessel to measure the oxygen concentration.

When the test method (B) is performed, it need only be performed with rat primary-cultured liver cells to be seeded having a cell density of $1.0 \times 10^3$ cells/$cm^2$ to $4.0 \times 10^3$ cells/$cm^2$, and the dissolved oxygen concentration need only be in the range described above for at least one point in the range of the cell density. That is, the dissolved oxygen concentration is not required to be in the range described above over the entire range of the cell density of $1.0 \times 10^3$ cells/$cm^2$ to $4.0 \times 10^3$ cells/$cm^2$.

The culture solution for rat primary-cultured liver cells used in the test method (B) is not particularly limited, and examples include a solution containing 10% fetal bovine serum (FBS, FUJIFILM Wako Pure Chemical Corporation), 30 mg/mL L-proline (for culture, FUJIFILM Wako Pure Chemical Corporation), $1 \times 10^{-7}$ M dexamethasone (for biochemistry, FUJIFILM Wako Pure Chemical Corporation), 50 μg/mL hydrocortisone (for culture, FUJIFILM Wako Pure Chemical Corporation), 20 ng/mL epidermal growth factor (EGF, for cell biology, FUJIFILM Wako Pure Chemical Corporation), $5.0 \times 10^{-7}$ M insulin (SIGMA), 5000 units/mL penicillin, 5000 µg/mL streptomycin (for culture, FUJIFILM Wako Pure Chemical Corporation), and D-MEM medium (containing high glucose, L-glutamine, phenol red, sodium pyruvate, and sodium hydrogen carbonate, for culture, FUJIFILM Wako Pure Chemical Corporation).

<Oxygen Consumption Rate>

The oxygen consumption rate can be calculated, using Fick's law, by dividing the product of the difference between the oxygen concentration (20%) of the outside air and the dissolved oxygen concentration in a culture solution and the oxygen permeation rate of a film by the cell density, as a consumption amount per cell. This is based on the concept that oxygen is supplied from the outside air for the amount of oxygen in the medium consumed by cells.

The appropriate oxygen consumption rate differs according to organs and cells that constituting the organs, for example, lung, heart, liver, kidney, spleen, pancreas, gallbladder, esophagus, stomach, skin, and brain. It also differs according to animal species, for example, humans, cattle, dogs, cats, pigs, miniature pigs, rabbits, hamsters, rats, and mice. Further, it differs between primary-cultured cells and subcultured established cell lines.

In the case of rat primary-cultured liver cells, when the cells are seeded in a cell culture vessel at $1.0 \times 10^5$ cells/cm$^2$, the oxygen consumption rate is 90 pmol/s/$10^5$ cells immediately after the cells attach to the culture vessel and 40 pmol/s/$10^5$ cells after that, according to Non Patent Literatures 2 and 3. The value may vary depending on the degree of attachment or aggregation of cells to the vessel.

The use of the culture material of the present invention enables culture in a suitable oxygen environment for cells, etc. When the cell density is, for example, $1.0 \times 10^3$ cells/cm$^2$, the oxygen consumption rate is preferably 40 pmol/s/$10^5$ cells or more, and more preferably 40 to 150 pmol/s/$10^5$ cells. When the oxygen consumption rate is evaluated, culture is preferably performed according to the test method (B) described above. That is, when the test method (B) is performed with rat primary-cultured liver cells to be seeded having a cell density of $1.0 \times 10^3$ cells/cm$^2$ to $4.0 \times 10^3$ cells/cm$^2$, the oxygen consumption rate is preferably 40 to 150 pmol/s/$10^5$ cells for at least one point in the range of the cell density.

<Culture Vessel>

A culture vessel of the second aspect of the present invention is a culture vessel in which at least a culture surface is formed of the culture material described above.

The culture vessel of the present invention may be the culture material described above itself or may be partly constituted of the culture material. When the culture vessel is partly constituted of the culture material, at least the surface with which cells or a scaffold material such as collagen is directly in contact is constituted of the culture material.

The culture vessel of the present invention is superior in shape stability and has sufficient oxygen supply to cells, etc. As the culture vessel, the shape and size are not particularly limited. Examples include a petri dish, a flask, an insert, a plate, a bottle, and a bag. The culture vessel preferably has at least one well. The culture vessel is preferably a plate having well(s), and more preferably a plate having well(s) such as 1 well, 6 wells, 12 wells, 24 wells, 48 wells. 96 wells, 384 wells, and 1536 wells.

The culture vessel of the present invention means a culture vessel in which the culture surface is not coated with a natural polymer material, a synthetic polymer material, or an inorganic material serving as a scaffold for cells, etc.

When the culture vessel is a petri dish, a flask, an insert, or a plate, the bottom surface is a culture surface. Therefore, among the bottom surface, the side surface, and the top surface of these culture vessels, at least a part or all of the bottom surface is preferably constituted of the culture material. When at least the bottom surface (culture surface) is constituted of the culture material of the present invention, it is possible to efficiently supply oxygen in the medium through the culture material and thereby efficiently proliferate cells, etc. in the medium. Further, the superior shape stability of the bottom surface allows cells, etc. to be uniformly cultured. Furthermore, the superior transparency facilitates observation of cells, etc.

The shape of the bottom surface is not particularly limited, and examples include a flat bottom, a round bottom (U-bottom), a flat bottom (F-bottom), a cone bottom (V-bottom), and a flat bottom+curved edge. When the bottom surface is processed to be a round bottom (U-bottom), a flat bottom (F-bottom), a cone bottom (V-bottom), a flat bottom+curved edge, or the like, it may be processed at once by general injection molding or press molding, or may be made by making a film or sheet in advance, followed by secondary processing such as vacuum molding and pressure molding. The shape of the bottom surface is selected according to the purpose of culture. For two-dimensional culture of cells, etc., the shape is preferably a flat bottom. For three-dimensional culture of cells, etc., the shape is preferably a flat bottom (U-bottom) or a cone bottom (V-bottom).

The portion other than the culture material of the culture vessel may be constituted of a material other than the culture material. The material other than the culture material is not particularly limited, and publicly known materials may be used. Examples include polyethylene (PE), polystyrene (PS), polydimethylsiloxane (PDMS), and glass.

The culture vessel of the present invention may be subjected to a disinfection/sterilization treatment to prevent contamination. A method for the disinfection/sterilization treatment is not particularly limited, and examples include physical disinfection methods such as a flowing steam method, a boiling method, an intermittent method, and an ultraviolet method; chemical disinfection methods using ozone or other gases or disinfectants such as ethanol; heat sterilization methods such as a high pressure steam method and a dry heat method; irradiation sterilization methods such as a gamma-ray method and a high-frequency method; and gas sterilization methods such as an ethylene oxide gas method and a hydrogen peroxide gas plasma method. Among them, due to simple operation and sufficient sterilization, an ethanol disinfection method, a high pressure steam sterilization method, a gamma-ray sterilization method, or an ethylene oxide gas sterilization method is preferable. These disinfection/sterilization treatments may be performed singly, or two or more of them may be performed in combination.

A method for producing the culture vessel of the present invention is not particularly limited. When the culture material is the culture vessel itself, the culture vessel may be produced in the method described above. When the culture vessel is partly formed of the culture material, it may be obtained by appropriately joining the culture material with other member. A joining method is not particularly limited, and the culture material and other member may be formed integrally or may be firmly attached together with an adhesive agent or a tackiness agent interposed therebetween.

The culture vessel of the present invention is preferably a culture vessel for cells, and preferably a culture vessel for liver cells.

<Culture Tool>

A culture tool of the third aspect of the present invention includes the culture material of the first aspect or the culture vessel of the second aspect. The culture tool of the present invention may be the culture material itself of the first aspect or the culture vessel itself of the second aspect, and may be a culture tool in which the culture surface of the culture material of the first aspect or the culture vessel of the second aspect is coated with a natural polymer material, a synthetic polymer material, or an inorganic material.

The coated culture tool may be obtained by, for example, coating the culture material with a natural polymer material, a synthetic polymer material, or an inorganic material by a publicly known method. The culture tool may be obtained by, for example, coating the culture vessel with a natural polymer material, a synthetic polymer material, or an inorganic material by a publicly known method, or using a culture material that has been coated with such a material in advance for at least the culture surface of the culture vessel.

The coated culture tool is superior in adhesion and proliferation of cells, etc. This is probably because the natural polymer material, the synthetic polymer material, or the inorganic material coated on the culture surface serves as a scaffold for cells, etc. Therefore, when adherent cells, etc. are cultured, usually the culture material or the culture vessel is coated with a natural polymer material, a synthetic polymer material, or an inorganic material and used as a culture tool.

The natural polymer material, the synthetic polymer material, and the inorganic material are not particularly limited. Examples of the natural polymer material include collagen, gelatin, alginic acid, glycosaminoglycan such as hyaluronic acid and chondroitin sulfate, fibronectin, laminin, fibrinogen, osteopontin, tenascin, vitronectin, thrombospondin, agarose, elastin, keratin, chitosan, fibrin, fibroin, and saccharides. Examples of the synthetic polymer material include polyglycolic acid, polylactic acid, polyethylene glycol, polycaprolactone, synthetic peptides, and synthetic proteins, polyhydroxyethyl methacrylate, and polyethlylenimine. Examples of the synthetic polymer material include polyethylene glycol, polyhydroxyethyl methacrylate, and polyelylenimine. Examples of the inorganic material include β-tricalcium phosphate and calcium carbonate.

Further, examples of the natural polymer material, the synthetic polymer material, and the inorganic material include a vitrigel obtained by subjecting a conventional hydrogel of extracellular matrix components or the like to vitrification, followed by rehydration. Further exemplified is, for example, a collagen vitrigel composed of the network of high-density collagen filaments made of collagen, which is one of extracellular matrix components.

To improve adhesion of cells and proliferation of cells and maintain the functions of cells for a longer period, coating with proteins such as collagen, gelatin, laminin, and polylysine, or peptides is preferable, and a coating treatment with collagen or polylysine is more preferable. These coatings may be performed singly, or two or more of them may be performed in combination.

The culture tool of the present invention is preferably a culture tool for cells, and more preferably a culture tool for liver cells.

<Culture Method>

A fourth aspect of the present invention is a method for culturing cells, tissues, or organs including a step of incubating cells, tissues, or organs in the culture tool of the third aspect.

The culture method of cells, etc. need only have a step of incubating cells, etc. in the culture tool, and other culture conditions may be appropriately selected according to the characteristics of the cells, etc. The culture method of cells, etc. is preferably a culture method of cells, and more preferably a culture method of liver cells.

EXAMPLES

Hereinafter, the present invention will be explained in detail with reference to Examples; however, it is not limited to these Examples.

The following items in Examples are described below: a method for measuring a polymer analysis value; a method for measuring a sagging distance; a method for measuring a water contact angle; a method for preparing a collagen coating solution; a cell type and a method for preparing a culture solution; a method for measuring a dissolved oxygen concentration in a medium; a method for calculating an oxygen consumption rate; a method for measuring a metabolism activity value; a method for evaluating cell adhesion; a method for observing autofluorescence of cultured cells; and evaluation of drug sorption.

[Weight Average Molecular Weight (Mw) and Molecular Weight Distribution (Mw/Mn)]

The weight average molecular weight (Mw) and the molecular weight distribution (Mw/Mn) of a 4-methyl-1-pentene polymer used as a culture material of the present invention were measured by gel permeation chromatography (GPC).

Specifically, in the conditions described below, the weight average molecular weight (Mw) and the number average molecular weight (Mn) of the polymer dissolved in orthodichlorobenzene were measured by calibrating the molecular weight based on polystyrene standards.

Apparatus: gel permeation chromatograph, model HLC-8321 GPC/HT (manufactured by Tosoh Corporation).

Data analysis software: Empower3 (manufactured by Waters Corporation)

Detector: differential refractometer

Columns connected in series: TSKgel GMH6-HT (2 columns) and TSKgel GMH6-HTL (2 columns)

Column temperature: 140° C.

flow rate: 1.0 ml/min

Sample concentration: 1.5 mg/ml

[Measurement of Sagging Distance]

A test piece was cut out in the size of 100 mm long and 10 mm wide. The test piece was fixed onto a test board in a state where the test piece protruded lengthwise a length of 50 mm in a horizontal direction from a top surface of the test board, the top surface being horizontal. Three minutes after fixing, a measurement was performed of a distance of how much an end of the test piece protruding from the test board sagged in a vertically downward direction from a horizontal plane including the top surface of the test board. The fixing to the measurement was performed at room temperature 23° C. The results are shown in Table 1.

[Measurement of Water Contact Angle]

The measurement of a water contact angle of a culture material after being subjected to a surface hydrophilic treatment can be performed by a method according to Japan Industrial Standard JIS-R3257 (Testing method of wettability of glass substrate) as follows: in the condition of constant temperature and humidity at 25±5° C. and 50±10%, a water droplet having a volume of 4 μL or less, the shape of which is deemed as a spherical shape, is added dropwise on a substrate surface; and the contact interface angle of the substrate and the water droplet within 1 minute after the water droplet is brought into contact with the substrate surface is measured according to the sessile drop method. In the present embodiment, the value within 1 minute after the water droplet was brought into contact with according to the method described above, was used as a physical property value.

[Preparation of Collagen Coating Solution]

A 0.1 M hydrochloric acid solution (for volumetric analysis, FUJIFILM Wako Pure Chemical Corporation) was diluted with water for injection (the Japanese Pharmacopoeia, Otsuka Pharmaceutical Co., Ltd.) by 100 times to prepare a 0.001 M hydrochloric acid solution, and subjected to filtration sterilization. A 3 mg/mL collagen solution (Cellmatrix type I-P, derived from porcine tendon, Nitta Gelatin) was diluted with a 0.001 M hydrochloric acid solution by 2 times to prepare a 1.5 mg/mL collagen coating solution.

[Cell Type and Method for Preparing Culture Solution]

A culture solution was added to a centrifuge tube (50 ml) to which a cell suspension containing rat cryopreserved hepatocytes had been added. As the culture solution, 1.5 ml of fetal bovine serum (FBS, FUJIFILM Wako Pure Chemical Corporation), 0.15 ml of L-proline (for culture, FUJIFILM Wako Pure Chemical Corporation) diluted to 3.0 g/mL with water for injection (Fuso Pharmaceutical Industries, Ltd.), 1.5 μL of a dexamethasone solution (for biochemistry, FUJIFILM Wako Pure Chemical Corporation) diluted to $1 \times 10^{-3}$ M with ethanol (for molecular biology, FUJIFILM Wako Pure Chemical Corporation), 21 μL of a hydrocortisone solution (for culture, FUJIFILM Wako Pure Chemical Corporation) diluted to 36 mM with ethanol, and a BSA solution diluted to 1.0 mg/mL with water for injection were used, and further 15 μL of an epidermal growth factor solution (EGF, for cell biology, FUJIFILM Wako Pure Chemical Corporation) diluted to 20 μg/mL, 8.7 μL of an insulin solution (10 mg/mL in HEPESS, SIGMA), 0.3 ml of a penicillin/streptomycin solution (containing 5000 units/mL penicillin and 5000 μg/mL streptomycin, for culture, FUJIFILM Wako Pure Chemical Corporation), and 13 ml of D-MEM medium (containing 4500 mg/mL D-glucose, 584 mg/mL L-glutamine, 15 mg/mL phenol red, 110 mg/mL sodium pyruvate, and 3700 mg/mL sodium hydrogen carbonate, for culture, FUJIFILM Wako Pure Chemical Corporation) were added for preparation. The adjustment of the cell density was performed by adjusting the number of cells in the cell suspension containing rat cryopreserved hepatocytes. Unless otherwise noted, the cell density was $1.0 \times 10^5$ cells/cm$^2$. In the high-density culture in Example 8 and Comparative Example 6, the cell density was $4.0 \times 10^5$ cells/cm$^2$.

[Measurement of Oxygen Permeation Coefficient and Calculation of Oxygen Permeation Rate]

The oxygen permeation coefficient was measured in an environment of a temperature of 23° C. and a humidity of 0% RH by a differential pressure gas permeability measuring apparatus MT-C3 manufactured by Toyo Seiki Seisaku-Sho, Ltd. The diameter of a measurement portion was 70 mm (the permeation area was 38.46 cm$^2$). Since a large oxygen permeation coefficient was expected, the sample was masked with aluminum foil in advance to have an actual permeation area of 5.0 cm$^2$.

The measured value of the oxygen permeation coefficient [cm$^3 \times$mm/(m$^2 \times$24 h$\times$atm)] was divided by the thickness (μm) of the film (culture material) to calculate the oxygen permeation rate [cm$^3$/(m$^2 \times$24 h$\times$atm)].

[Measurement of Dissolved Oxygen Concentration in Medium]

One day after seeding cells, the culture solution was removed from the culture vessel, and 0.5 ml of the culture solution was newly added. Then, the dissolved oxygen concentration in the culture solution was measured using a FireSting oxygen monitor (manufactured by BAS Inc.). The measurement was performed in a humidified incubator. A sensor was placed at 80 μm height from a bottom surface of the culture vessel, and the dissolved oxygen concentration was measured for 1 hour. The value (%) obtained by dividing the dissolved oxygen concentration after 1 hour by the saturated oxygen concentration in the culture solution and multiplying by 100 is shown in Table 1. The saturated oxygen concentration in the culture solution was measured by a fluorescence oxygen sensor (FireSting oxygen monitor, manufactured by BAS Inc.).

[Calculation of Oxygen Consumption Rate]

The oxygen consumption rate was calculated by dividing the product of the difference between the oxygen concentration (20%) of the outside air (inside the humidified incubator) and the dissolved oxygen concentration in the culture solution as described above and the oxygen permeation rate by the cell density, as a consumption amount per cell.

[Measurement of Metabolism Activity Value]

Twenty four hours after seeding cells, the culture solution was removed from the culture vessel, luciferin-CEE diluted with the culture solution was added, and the cells were further cultured for 3 hours. After the cultured cells were transferred to a 96-well plate together with the culture solution containing luciferin-CEE, a liquid mixture of a luciferin detection reagent and a reconstitution buffer was added and allowed to react for 1 hour at room temperature with light shielded. After 1 hour, the amount of luminescence (relative light unit: RLU) was measured with a luminometer.

For the amount of protein, the followings were performed. After the luciferin-CEE solution diluted with the culture solution was removed, 200 μL of PBS(−) was added to the medium, and then cells were recovered in an Eppendorf tube using a cell scraper and centrifuged (4° C., 22000×g, 10 minutes). Subsequently, the supernatant was removed, and 100 μL of a 0.1 M sodium hydroxide solution was added. Then, the amount of protein was measured using Pierce (trademark) BCA Protein Assay Kit (Thermo Fisher Scientific). The absorbance at wavelength 450 nm was measured with a plate reader (SPECTRA max PLUS384, manufactured by Molecular Devices, LLC.).

The metabolism activity amount (pmol/L) of the luciferin-CEE solution, which was obtained with a luminometer, was measured using P450-Glo (trademark) CYP1 A1 Assay kit (Promega), and divided by the amount of protein obtained by the absorbance and the reaction time of the luciferin-CEE solution to calculate the metabolism activity value (pmol/min/mg protein). The results are shown in Table 1.

[Evaluation of Cell Adhesion]

The cell suspension (0.5 ml) of rat cryopreserved hepatocytes was seeded in a vessel and incubated at 37° C. under 5% $CO_2$. After the culture for 1 day and 7 days, the cells were observed with a microscope for evaluation of cell adhesion. Table 1 shows that the state where the hepatocytes adhere and extend is indicated as AA, the state where the hepatocytes adhere and slightly extend is indicated as BB, and the state where the hepatocytes adhere but are round and do not extend or the hepatocytes have fallen away is indicated as CC.

[Observation of Autofluorescence in Culture Vessel]

An All-in-One Fluorescence microscope BZ-X700 (manufactured by KEYENCE CORPORATION) was used. Via accessory filters of the microscope called BZ-X filter DAPI (blue coloration), BZ-X filter GFP (green coloration), and BZ-X filter TexasRed (red coloration), the culture material at the bottom surface of the culture vessel was observed, and occurrence or not of fluorescent colors blue, green, and red was observed.

[Evaluation of Drug Sorption]

Various types of drug solutions were each added to freely-selected three wells in a 24-well vessel in an amount of 0.5 ml to each well and left to stand at 23° C. for 2 days. Thereafter, the drug solutions were recovered. The concentrations of the recovered drug solutions were measured by a fluorescence analysis method or LC/MS. The drug residual rate, which was the concentration of the measured recovered drug solution with respect to the concentration of the drug solution before added to the vessel, was calculated. The average value of the drug residual rate in three wells was given.

Drugs for Evaluation

1. A solution of rhodamine B in phosphate buffered saline (hereinafter, referred to as PBS) (concentration 10 µmol/L)
2. A solution of rhodamine 123 in PBS (concentration 10 µmol/L)
3. A solution of rhodamine 6G in PBS (concentration 10 µmol/L)
4. A solution of cyclosporin A in dimethyl sulfoxide (hereinafter, referred to as DMSO) (concentration 10 µmol/L)
5. A solution of ticlopidine hydrochloride in DMSO (concentration 10 µmol/L)
6. A solution of leflunomide in DMSO (concentration 10 µmol/L)
7. A solution of troglitazone in DMSO (concentration 10 µmol/L)
8. A solution of isoproterenol hydrochloride in DMSO (concentration 10 µmol/L)

For the drugs 1 to 3 for evaluation, concentration analysis was performed by a fluorescence analysis method. For the drugs 4 to 8 for evaluation, concentration analysis was performed by LC/MS.

<Fluorescence Analysis Conditions>
Evaluation apparatus: FP-6600 (spectrofluorometer, manufactured by JASCO Corporation)
Used cell: Micro cell made of quartz
Bandwidth: excitation side: 5 nm, fluorescence side: 6 nm
Sensitivity (PMT voltage): 400 V
Excitation wavelength: rhodamine B 555 nm
  rhodamine 123 505 nm
  rhodamine 6G 525 nm
Fluorescence measurement wavelength: rhodamine B 580 nm
  rhodamine 123 530 nm
  rhodamine 6G 555 nm
Scanning speed: 2000 nm/min <LC/MS Conditions>
Apparatus: Acquity UPLC I-class system/TQ-S micro (water)
Ionization method: electrospray ionization (ESI), positive and negative ion detection
Detection: selected reaction monitoring (SRM)

1. Polarity:
  Positive: cyclosporin A, ticlopidine hydrochloride, isoproterenol hydrochloride
  Negative: leflunomide, troglitazone
2. Precursor Ion:
  cyclosporin A: m/z1203
  ticlopidine hydrochloride: m/z264
  leflunomide: m/z269
  troglitazone: m/z440
  isoproterenol hydrochloride: m/z212
3. Product Ion
  cyclosporin A: m/z156
  ticlopidine hydrochloride: m/z89
  leflunomide: m/z82
  troglitazone: m/z42
  isoproterenol hydrochloride: m/z152

[Production Example 1] Method for Producing Culture Material

TPX (registered trademark) (manufactured by Mitsui Chemicals, Inc.: molecular weight (Mw)=428000, molecular weight distribution (Mw/Mn)=4.1), which was a 4-methyl-1-pentene polymer, was used. Extrusion molding was performed by discharging TPX into a T-die extruder equipped with a screw of full flight type for extrusion of a substrate layer, setting the extrusion temperature to 270° C. and the roll temperature to 60° C., and changing the conditions of the roll rotational speed. Thus, five kinds of films having different thicknesses from each other were obtained. The films of thickness 50 µm, 100 µm, 200 µm, 280 µm, and 400 µm were respectively designated as Film 1, Film 2, Film 3, Film 4, and Film 5.

[Production Example 2] Surface Treatment Method of Culture Material and Production Method of Simple Culture Vessel Films 1 to 5 were subjected to a corona treatment by using a table-type corona treatment apparatus (manufactured by KASUGA DENKI, INC.) (treatment speed 3 m/min, output 0.5 kW, reciprocation 2 times). At this time, the water contact angle of the surface of the culture material was measured and shown in Table 1.

Thereafter, Films 1 to 5 were each cut out with a punch of 23 mm diameter and immersed with ethanol for disinfection (the Japanese Pharmacopoeia, FUJIFILM Wako Pure Chemical Corporation) for 1 hour. After 1 hour, Films 1 to 5 were immersed with Dulbecco's PBS(−) (for culture, FUJIFILM Wako Pure Chemical Corporation) in order to remove ethanol attached to the surface, and then dried overnight at room temperature for sterilization. The top surface and the bottom surface of each of Films 1 to 5 were sandwiched between sterilized polyethylene frames. In this manner, Culture vessels 1 to 5 in which the culture surface was 15 mm in inner diameter were prepared.

[Production Example 3] Surface Treatment Method of Culture Material and Production Method of 24-Well Culture Plate Film 1 was subjected to a plasma treatment by using an atmospheric-pressure plasma surface treatment apparatus (manufactured by Sekisui Chemical Company, Limited) and filling the inside of the chamber with nitrogen gas stream (treatment speed 2 m/min, output 4.5 kW, reciprocation 2 times). At this time, the water contact angle of the surface of the culture material was measured and shown in Table 1.

Thereafter, Film 1 that had been subjected to a plasma treatment was firmly attached to the bottom surface of a 24-well vessel frame made of polystyrene (also referred to as PS) with a tackiness agent for medical use interposed therebetween. In this manner, a 24-well culture plate (Culture vessel 6) was prepared, further packed in a gamma-ray-resistant bag, and sterilized by irradiation with gamma-rays of 10 kGy.

Example 1

After 0.5 ml of the 1.5 mg/mL collagen coating solution was added to the culture surface of Culture vessel 1 prepared with Film 1 having a thickness of 50 µm, excess collagen coating solution was removed. Culture vessel 1 was left to stand at room temperature for 30 to 60 minutes, washed with the Dulbecco's PBS(−), and dried overnight at room temperature. In the same manner, five of collagen-coated Culture vessels 1 were prepared.

Next, the culture solution (0.5 mL) containing the rat cryopreserved hepatocytes was seeded on the culture surface of each of five Culture vessels 1 with a micropipette. Then, Culture vessels 1 were each covered with a lid made of polystyrene and placed in an incubator to start culture at 37° C. under 5% $CO_2$. After 1 day, four Culture vessels 1 were taken out of the incubator, the bottom surface of each vessel was viewed laterally, and the presence or absence of sagging of the film in the culture environment was observed. As a result, all vessels showed no change from the time when vessels were prepared and no sagging. Next, each of four Culture vessels 1 was observed with a microscope, and the appearance of cells expanding while adhering to the vessel was observed. Thereafter, with one out of four Culture vessels 1, the dissolved oxygen concentration in the medium was measured, and the oxygen consumption rate was calculated. With the remaining three, the metabolism activity was measured, and the result is shown in Table 1. (The metabolism activity value is shown in Table 1 as the average value of results of the three vessels.) Further, the remaining one vessel was cultured for 7 days and taken out of the incubator. The appearance of cells expanding while adhering to the vessel was observed, and the result is shown in Table 1. FIG. 1 shows the results of observation of cells after 1 day and 7 days with a phase-contrast microscope.

Example 2

Rat cryopreserved hepatocytes were cultured in the same manner as in Example 1, except for using Culture vessel 2 prepared with Film 2 having a thickness of 100 µm. After 1 day, the bottom surface of each vessel was viewed laterally, and the presence or absence of sagging of the film in the culture environment was observed. As a result, the film showed no change from the time when vessels were prepared and no sagging. Table 1 shows results for evaluation of cell adhesion, the calculation result of the oxygen consumption rate from the dissolved oxygen concentration, and the measured value of metabolism activity after 1 day culture and cell adhesion after 7 days culture.

Example 3

Rat cryopreserved hepatocytes were cultured in the same manner as in Example 1, except for using Culture vessel 3 prepared with Film 3 having a thickness of 200 µm. After 1 day, the bottom surface of each vessel was viewed laterally, and the presence or absence of sagging of the film in the culture environment was observed. As a result, the film showed no change from the time when vessels were prepared and no sagging. Table 1 shows results for evaluation of cell adhesion, the calculation result of the oxygen consumption rate from the dissolved oxygen concentration, and the measured value of metabolism activity after 1 day culture and cell adhesion after 7 days culture.

Example 4

Rat cryopreserved hepatocytes were cultured in the same manner as in Example 1, except for using Culture vessel 4 prepared with Film 4 having a thickness of 280 µm. After 1 day, the bottom surface of each vessel was viewed laterally, and the presence or absence of sagging of the film in the culture environment was observed. As a result, the film showed no change from the time when vessels were prepared and no sagging. Table 1 shows results for evaluation of cell adhesion, the calculation result of the oxygen consumption rate from the dissolved oxygen concentration, and the measured value of metabolism activity after 1 day culture and cell adhesion after 7 days culture.

Example 5

Rat cryopreserved hepatocytes were cultured in the same manner as in Example 1, except for using Culture vessel 5 prepared with Film 5 having a thickness of 400 µm. After 1 day, the bottom surface of each vessel was viewed laterally, and the presence or absence of sagging of the film in the culture environment was observed. As a result, the film showed no change from the time when vessels were prepared and no sagging. Table 1 shows results for evaluation of cell adhesion, the calculation result of the oxygen consumption rate from the dissolved oxygen concentration, and the measured value of metabolism activity after 1 day culture and cell adhesion after 7 days culture.

Example 6

Rat cryopreserved hepatocytes were cultured in the same manner as in Example 1, except for using Culture vessel 6, which was a 24-well culture plate prepared in Production Example 3. At that time, four out of 24 wells were used. After 1 day, the bottom surface of each vessel was viewed laterally, and the presence or absence of sagging of the film in the culture environment was observed. As a result, the film showed no change from the time when vessels were prepared and no sagging. Table 1 shows results for evaluation of cell adhesion, the calculation result of the oxygen consumption rate from the dissolved oxygen concentration, and the measured value of metabolism activity after 1 day culture and cell adhesion after 7 days culture.

Example 7

Rat cryopreserved hepatocytes were cultured in the same manner as in Example 1, except for using Culture vessel 6, which was a 24-well culture plate prepared in Production Example 3, not subjected to collagen coating, and seeding the culture solution (0.5 mL) containing the rat cryopreserved hepatocytes directly on each of four wells of Culture vessel 6. After 1 day, the bottom surface of each vessel was viewed laterally, and the presence or absence of sagging of the film in the culture environment was observed. As a result, the film showed no change from the time when vessels were prepared and no sagging. Table 1 shows results for evaluation of cell adhesion, the calculation result of the oxygen consumption rate from the dissolved oxygen concentration, and the measured value of metabolism activity after 1 day culture and cell adhesion after 7 days culture.

Example 8

Rat cryopreserved hepatocytes were cultured in the same manner as in Example 1, except for changing the cell density in the culture solution to $4.0 \times 10^3$ cells/cm$^2$. After 1 day, the bottom surface of each vessel was viewed laterally, and the presence or absence of sagging of the film in the culture environment was observed. As a result, the film showed no change from the time when vessels were prepared and no sagging. Table 1 shows results for evaluation of cell adhesion, the calculation result of the oxygen consumption rate from the dissolved oxygen concentration, and the measured value of metabolism activity after 1 day culture and cell adhesion after 7 days culture.

Example 9

Film 6 having a thickness of 50 μm was obtained in the same manner as in Production Example 1, except for using TPX (registered trademark) (manufactured by Mitsui Chemicals, Inc.) having a weight average molecular weight (Mw) of 95000 and a molecular weight distribution (Mw/Mn) of 3.5, which was a 4-methyl-1-pentene polymer.

Rat cryopreserved hepatocytes were cultured in the same manner as in Example 1, except for changing Film 1 to Film 6. After 1 day, the bottom surface of each vessel was viewed laterally, and the presence or absence of sagging of the film in the culture environment was observed. As a result, the film showed no change from the time when vessels were prepared and no sagging. Table 1 shows results for evaluation of cell adhesion, the calculation result of the oxygen consumption rate from the dissolved oxygen concentration, and the measured value of metabolism activity after 1 day culture and cell adhesion after 7 days culture.

Example 10

Figure 4:
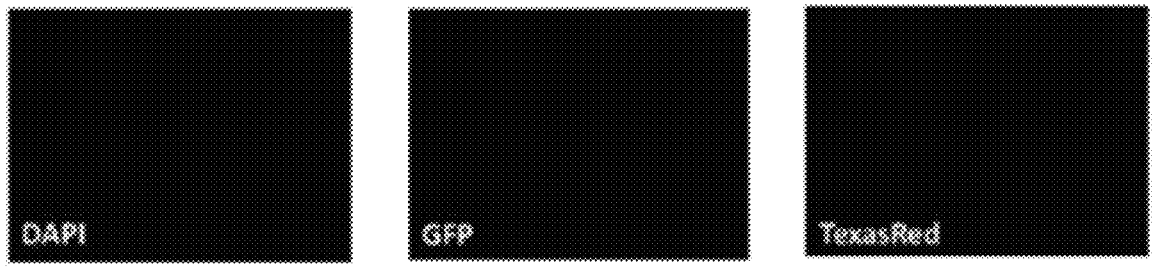
FIG. 4 shows photographs of a culture material of Example 10 observed with a fluorescence microscope (left: DAPI filter, middle: GFP filter, right: TexasRed filter).

The bottom surface of the culture vessel of Example 5, in which the culture material was a 4-methyl-1-pentene polymer, was observed with a fluorescence microscope to confirm occurrence or not of autofluorescence derived from the culture material. As a result, no autofluorescence derived from the material was seen in observing with any of wavelength filters of BZ-X filter DAPI, BZ-X filter GFP, and BZ-X filter TexasRed. This revealed that cells can be observed directly on the culture surface of this vessel. FIG. 4 shows photographs of the culture surface observed with a fluorescence microscope.

Comparative Example 1

Culture vessel c1 was prepared by preparing Film having a thickness of 600 μm in the same manner as in Production Example 1, and subjecting Film to a surface treatment and sterilization in the same manner as in Production Example 2. Next, rat cryopreserved hepatocytes were cultured in the same manner as in Example 1. After 24 hours, the bottom surface of each vessel was viewed laterally, and the presence or absence of sagging of the film in the culture environment was observed. As a result, the film showed no change from the time when vessels were prepared and no sagging. Table 1 shows results for evaluation of cell adhesion, the calculation result of the oxygen consumption rate from the dissolved oxygen concentration, and the measured value of metabolism activity after 1 day culture and cell adhesion after 7 days culture.

Comparative Example 2

Culture vessel c2 was prepared by using Film 1 having a thickness of 50 μm and being subjected to sterilization with no surface treatment in Production Example 2. Next, Culture vessels c2 were subjected to collagen coating according to Example 1. However, the culture surface repelled the solution containing collagen and was unable to have collagen coating, leading to no culture of rat cryopreserved hepatocytes.

Comparative Example 3

Culture vessels c2 made in Comparative Example 2 were used. Culture vessels c2 were not subjected to collagen coating, directly seeded with the culture solution (0.5 mL) containing the rat cryopreserved hepatocytes, each covered with a lid made of polystyrene, and placed in an incubator to start culture at 37° C. under 5% $CO_2$. After 1 day, Culture vessels c2 were taken out of the incubator, the bottom surface of each vessel was viewed laterally, and the presence or absence of sagging of the film in the culture environment was observed. As a result, the film showed no change from the time when vessels were prepared and no sagging. Next, when the medium was removed for evaluation of the dissolved oxygen concentration and metabolism activity, cells had not been firmly fixed on the culture surface and were removed from the vessel together with the medium, and only a small number of cells remained on the culture surface. Therefore, it was not possible to evaluate the dissolved oxygen concentration and metabolism activity. The evaluation to be performed after 7 days was cancelled.

Comparative Example 4

Figure 2:
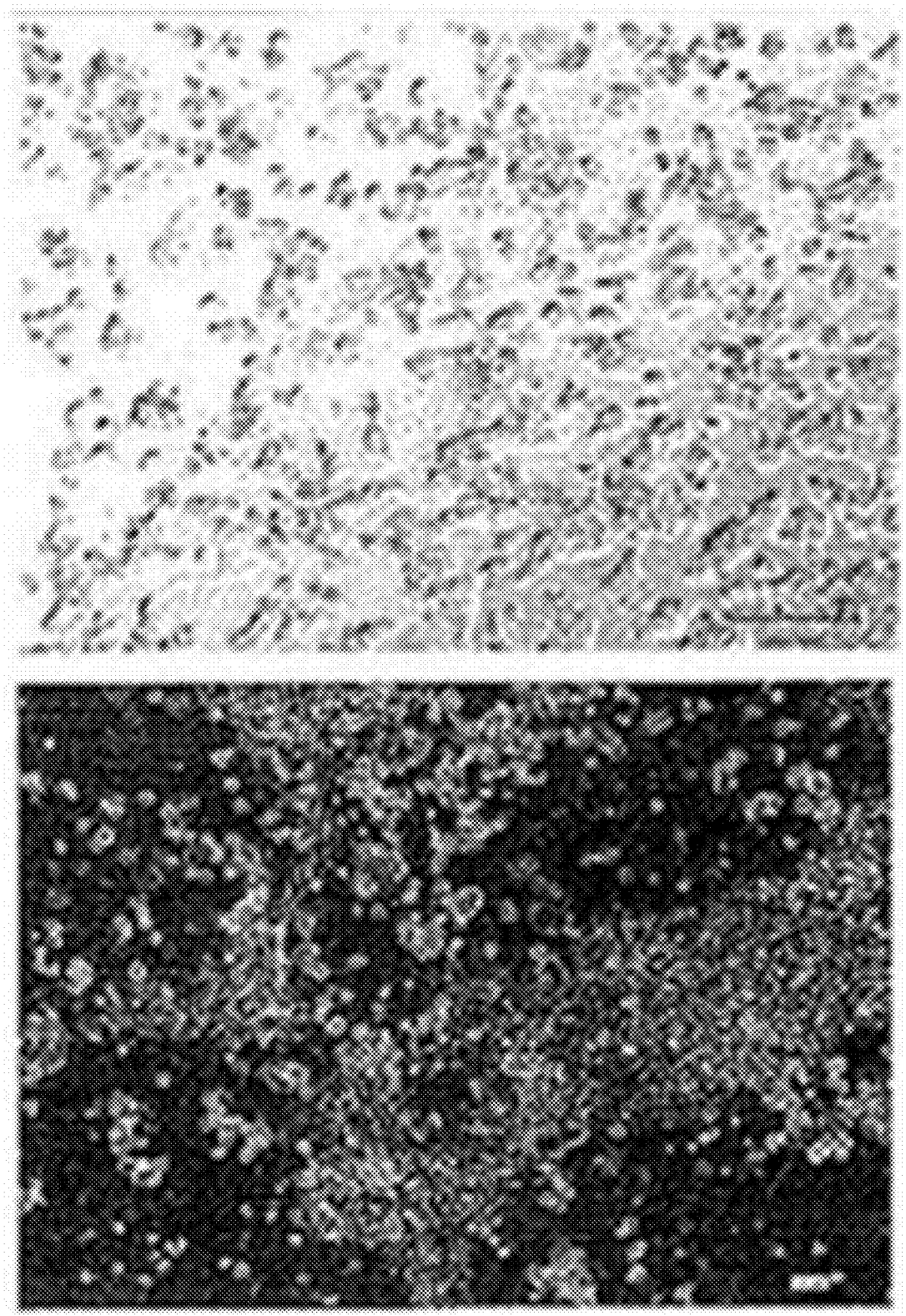
FIG. 2 shows photographs of cells of Comparative Example 4 observed with a phase-contrast microscope (upper: 1 day after, lower: 7 days after).

Rat cryopreserved hepatocytes were cultured in the same manner as in Example 1, except for using a commercially available 24-well TCPS culture vessel (manufactured by Corning Incorporated, made of polystyrene (PS)) having a culture surface thickness of 1000 μm. After 1 day, the bottom surface of each vessel was viewed laterally, and the presence or absence of sagging of the film in the culture environment was observed. As a result, the film showed no change from the time when vessels were prepared and no sagging. Table 1 shows results for evaluation of cell adhesion, the calculation result of the oxygen consumption rate from the dissolved oxygen concentration, and the measured value of metabolism activity after 1 day culture and cell adhesion after 7 days culture. FIG. 2 shows the results of observation of cells after 1 day and 7 days with a phase-contrast microscope.

Comparative Example 5

Figure 3:
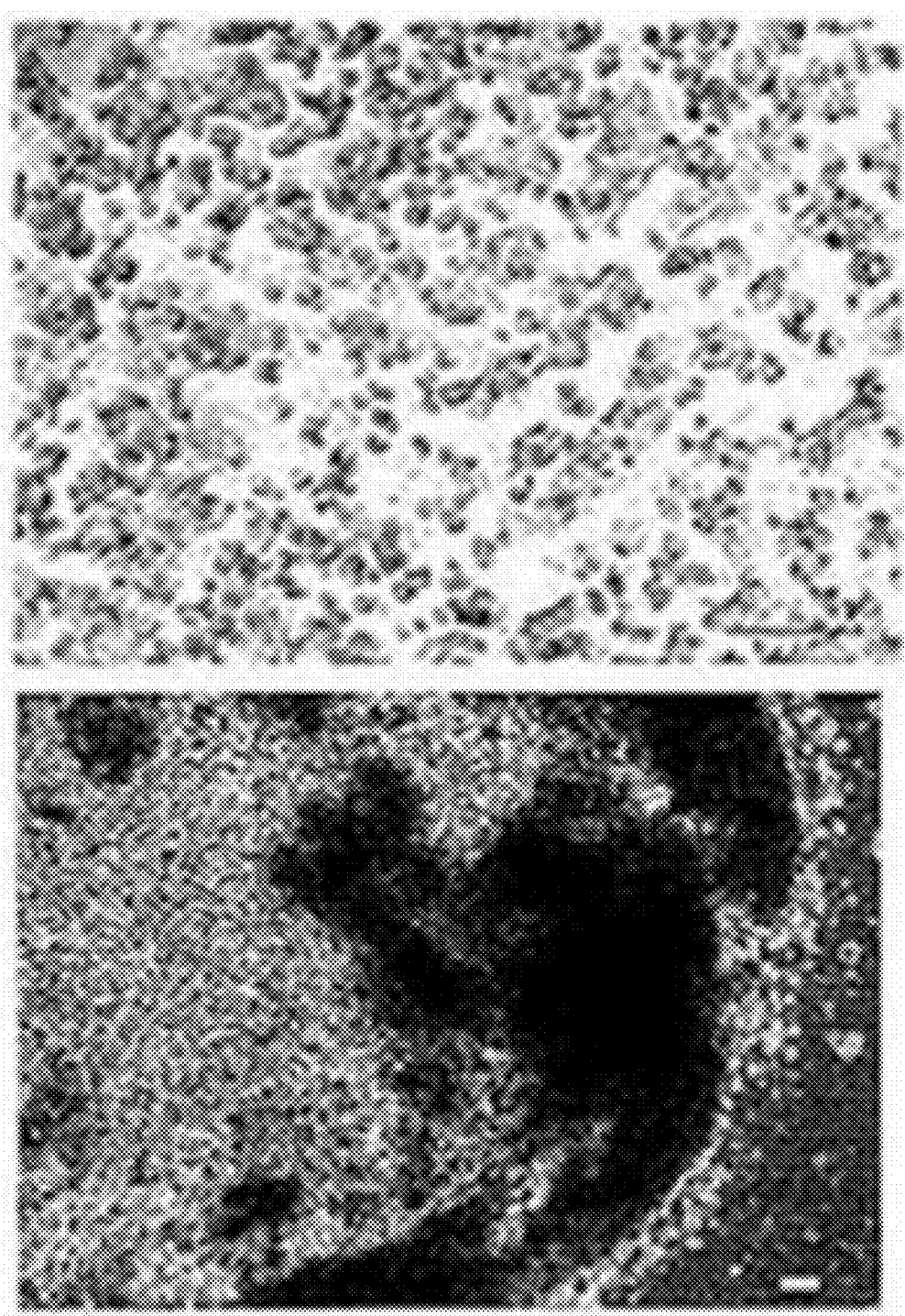
FIG. 3 shows photographs of cells of Comparative Example 5 observed with a phase-contrast microscope (upper: 1 day after, lower: 7 days after).

Rat cryopreserved hepatocytes were cultured in the same manner as in Example 1, except for using a commercially available 24-well PDMS (polydimethylsiloxane) culture vessel (product name: G-plate, VECELL (trademark) model number: V24WGPB-10) having a culture material thickness of 350 μm as a high-oxygen permeation vessel. After 1 day, the vessels were taken out of the incubator, the bottom surface of each vessel was viewed laterally, and the presence or absence of sagging of the film in the culture environment was observed. As a result, the film changed into a state where it warped and was sagging in a downward direction. When the medium was removed for evaluation of the dissolved oxygen concentration and metabolism activity, cells had proliferated in a state of clusters at the center of the culture surface. Table 1 shows results for evaluation of cell adhesion, the calculation result of the oxygen consumption rate from the dissolved oxygen concentration, and the measured value of metabolism activity after 1 day culture and cell adhesion after 7 days culture. FIG. 3 shows the results of observation of cells after 1 day and 7 days with a phase-contrast microscope.

Comparative Example 6

Rat cryopreserved hepatocytes were cultured in the same manner as in Example 1, except for using the 24-well TCPS culture vessel (manufactured by Corning Incorporated, made of polystyrene (PS)) described in Comparative Example 4 and changing the cell density in the culture solution to $4.0 \times 10^3$ cells/cm$^2$. After 1 day, the bottom surface of each vessel was viewed laterally, and the presence or absence of sagging of the film in the culture environment was observed. As a result, the film showed no change from the time when vessels were prepared and no sagging. Table 1 shows results for evaluation of cell adhesion, the calculation result of the oxygen consumption rate from the dissolved oxygen concentration, and the measured value of metabolism activity after 1 day culture and cell adhesion after 7 days culture.

Comparative Example 7

Figure 5:
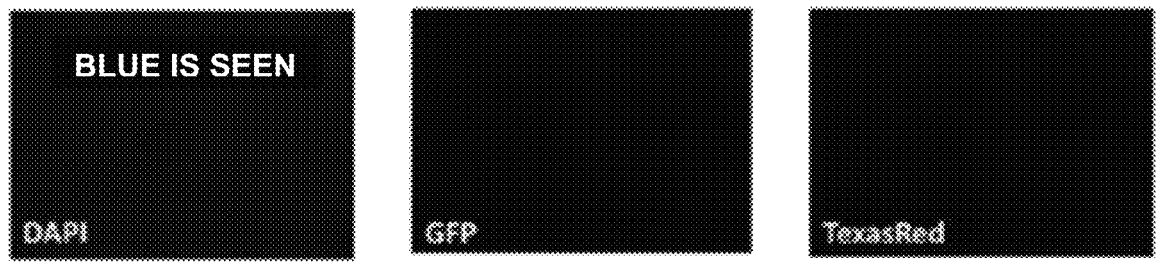
FIG. 5 shows photographs of a culture material of Comparative Example 6 observed with a fluorescence microscope (left: DAPI filter, middle: GFP filter, right: TexasRed filter).

The bottom surface of the culture vessel of Comparative Example 4, in which the culture material was polystyrene, was observed with a fluorescence microscope. As a result, no autofluorescence derived from the material was seen in observing with wavelength filters of BZ-X filter GFP and BZ-X filter TexasRed, but blue fluorescence derived from the material was seen in observing with a wavelength filter of BZ-X filter DAPI. This revealed that cells cannot be fluorescently observed directly in this culture vessel. FIG. 5 shows photographs of the culture surface observed with a fluorescence microscope.

TABLE 1

| Physical Properties | | Example 1 | Example 2 | Example 3 | Example 4 | Example 5 |
|---|---|---|---|---|---|---|
| Material | | 4-methyl-1-pentene Polymer | | | | |
| Mw × 10000 (Mw/Mn) | | 42.8 (4.1) | 42.8 (4.1) | 42.8 (4.1) | 42.8 (4.1) | 42.8 (4.1) |
| Surface Treatment | | Yes (Corona) | Yes (Corona) | Yes (Corona) | Yes (Corona) | Yes (Corona) |
| Collagen Coating | | Yes | Yes | Yes | Yes | Yes |
| Thickness | μm | 50 | 100 | 200 | 280 | 400 |
| Sagging Distance | mm | 0 | 0 | 0 | 0 | 0 |
| Presence or Absence of Warping | | No | No | No | No | No |
| Water Contact Angle | Degree | 72.9 | 67.7 | 80.2 | 65.1 | 60.7 |
| Cell Density | cells/cm$^2$ | $1.0 \times 10^5$ | $1.0 \times 10^5$ | $1.0 \times 10^5$ | $1.0 \times 10^5$ | $1.0 \times 10^5$ |
| Oxygen Permeation Coefficient | cm$^3$*mm/m$^2$*24 h*atm | 1912 | 1912 | 1912 | 1912 | 1912 |
| Oxygen Permeation Rate | cm$^3$/m$^2$*24 h*atm | 38240 | 19120 | 9560 | 6829 | 4780 |
| Cell Adhesion After 1 Day Culture | | AA | AA | AA | AA | AA |
| Cell Adhesion After 7 Days Culture | | AA | AA | AA | AA | AA |
| Dissolved Oxygen Concentration in Medium | % | 13.9 | 12.7 | 12.9 | 8.8 | 5.8 |
| Oxygen Consumption Rate | pmol/s/10$^5$ cells | 125.9 | 77.2 | 40.1 | 47.8 | 45.2 |
| Metabolism Activity Value | pmol/min/mg protein | 0.95 | 0.92 | 0.91 | 0.94 | 0.83 |

| Physical Properties | | Example 6 | Example 7 | Example 8 | Example 9 | Comparative Example 1 |
|---|---|---|---|---|---|---|
| Material | | 4-methyl-1-pentene Polymer | | | | |
| Mw × 10000 (Mw/Mn) | | 42.8 (4.1) | 42.8 (4.1) | 42.8 (4.1) | 9.5 (3.5) | 42.8 (4.1) |
| Surface Treatment | | Yes (Plasma) | Yes (Plasma) | Yes (Corona) | Yes (Corona) | Yes (Corona) |
| Collagen Coating | | Yes | No | Yes | Yes | Yes |
| Thickness | μm | 50 | 50 | 50 | 50 | 600 |
| Sagging Distance | mm | 0 | 0 | 0 | 0 | 0 |
| Presence or Absence of Warping | | No | No | No | No | No |
| Water Contact Angle | Degree | 52.3 | 52.3 | 72.9 | 72.9 | 38.8 |
| Cell Density | cells/cm$^2$ | $1.0 \times 10^5$ | $1.0 \times 10^5$ | $4.0 \times 10^5$ | $1.0 \times 10^5$ | $1.0 \times 10^5$ |
| Oxygen Permeation Coefficient | cm$^3$*mm/m$^2$*24 h*atm | 1912 | 1912 | 1912 | 1975 | 1912 |
| Oxygen Permeation Rate | cm$^3$/m$^2$*24 h*atm | 38240 | 38240 | 38240 | 39500 | 3187 |
| Cell Adhesion After 1 Day Culture | | AA | BB | AA | AA | AA |
| Cell Adhesion After 7 Days Culture | | AA | BB | AA | AA | AA |

TABLE 1-continued

| Physical Properties | | | | | | |
|---|---|---|---|---|---|---|
| Dissolved Oxygen Concentration in Medium | % | 13.5 | 14.6 | 12.2 | 13.9 | 8.2 |
| Oxygen Consumption Rate | pmol/s/$10^5$ cells | 128.3 | 110.5 | 40.2 | 125.9 | 27.9 |
| Metabolism Activity Value | pmol/min/mg protein | 0.97 | 0.85 | 1.02 | 0.95 | 0.70 |

| Physical Properties | | Comparative Example 2 | Comparative Example 3 | Comparative Example 4 | Comparative Example 5 | Comparative Example 6 |
|---|---|---|---|---|---|---|
| Material | | 4-methyl-1-pentene Polymer | 4-methyl-1-pentene Polymer | PS | PDMS | PS |
| Mw × 10000 (Mw/Mn) | | 42.8 (4.1) | 42.8 (4.1) | — | — | — |
| Surface Treatment | | No | No | Yes | Yes | Yes |
| Collagen Coating | | No | No | Yes | Yes | Yes |
| Thickness | μm | 50 | 50 | 1000 | 350 | 1000 |
| Sagging Distance | mm | 0 | 0 | 0 | 48 | 0 |
| Presence or Absence of Warping | | No | No | No | Yes | No |
| Water Contact Angle | Degree | 110 | 110 | 60.6 | 76.6 | 60.6 |
| Cell Density | cells/cm$^2$ | 1.0 × $10^5$ | 1.0 × $10^5$ | 1.0 × $10^5$ | 1.0 × $10^5$ | 4.0 × $10^5$ |
| Oxygen Permeation Coefficient | cm$^3$*mm/m$^2$*24 h*atm | 1912 | 1912 | 203 | 19121 | 203 |
| Oxygen Permeation Rate | cm$^3$/m$^2$*24 h*atm | 38240 | 38240 | 203 | 54631 | 203 |
| Cell Adhesion After 1 Day Culture | | CC | CC | AA | AA | AA |
| Cell Adhesion After 7 Days Culture | | —[1] | —[2] | AA | CC | AA |
| Dissolved Oxygen Concentration in Medium | % | —[1] | —[2] | 0.2 | 17.2 | 9.4 |
| Oxygen Consumption Rate | pmol/s/$10^5$ cells | —[1] | —[2] | 16.4 | 133.3 | 2.2 |
| Metabolism Activity Value | pmol/min/mg protein | —[1] | —[2] | 0.64 | 0.13 | 0.13 |

[1] Collagen coating was not possible, and cells did not adhere, leading to no culture
[2] When medium was removed, cells were removed from vessel together with medium, leading to no evaluation.

As seen from Table 1, long-term culture up to 7 days was possible in the culture of rat cryopreserved hepatocytes using the culture vessel in which the culture material of the present invention was placed at the bottom portion of the culture vessel. With no warping at the bottom surface of the vessel, cells uniformly adhered and proliferated over the entire culture surface and maintained the morphology. The bottom surface of the vessel showed no warping and kept sufficient strength even when Film 6 having a molecular weight (Mw) of 95000 and a thickness of 50 μm was used as a culture material. Thus, the culture material containing the 4-methyl-1-pentene polymer (X) of the present invention had superior shape stability.

From the detailed observation on the effect of culture of rat cryopreserved hepatocytes using the culture material of the present invention, the oxygen consumption rate of cells calculated by measuring the oxygen concentration in the medium after 1 day culture was 40 μmol/s/$10^5$ cells or more, and sufficient oxygen consumption rate was maintained even in the result with the cell density increased by 4 times. Thus, oxygen was supplied efficiently through the culture material. Accordingly, the metabolism activity value, which evaluated drug metabolism activity as a function of liver cells, was high, and the cell function was maintained normally. On the other hand, the oxygen consumption amounts in Comparative Examples 1 and 4 were less than 30 μmol/s/$10^5$ cells. Thus, oxygen that was necessary for rat cryopreserved hepatocytes to at least proliferate and express the function was not supplied. Accordingly, cells that were cultured especially in PS vessels in Comparative Examples 4 and 6 had low metabolism activity values, and even when cells proliferated, they were not able to express the normal function.

Further, the result of using the culture vessel in which PDMS, which was widely known as a high-oxygen permeation vessel, was placed on the bottom surface of the vessel (Comparative Example 5) showed that, PDMS on the bottom surface of the vessel largely warped in shape after 1 day despite of the not-so-large inner diameter, 16 mm, of a hole. This is presumed because the PDMS film has a sagging distance of 48 mm and easily warps. At this time, cells gathered in a state of clusters at the center of the bottom surface of the vessel. The metabolism activity value was confirmed and was very low. Defects are expected, such as occurrence of the difference in denseness and sparseness of cell density between cells in clusters and oxygen deficiency in the dense state. In addition, material-derived defects are conceived, such as the effect of poisoning from the remaining monomer of PDMS.

Further, for the surface characteristics of the culture material of the present invention, in either case of when cells were directly seeded on the surface of the culture material and cultured or when cells were subjected to collagen coating and cultured, cells and/or collagen firmly attached to the surface of the culture material in a good state. The results shown in Comparative Examples 2 and 3 shows that at least in the culture of the present embodiment using collagen or cells, the surface of the culture material is required to be hydrophilic (have a certain water contact angle). A wide variety of cells are known, and various culture methods are also known according to cells and purposes these days. In such a state, the hydrophilic treatment of the surface of the culture material is regarded as a useful method as one means for using the oxygen-permeable vessel of the present invention.

Example 11

A drug sorption test was performed on the 4-methyl-1-pentene polymer vessel used in Example 6. The results are shown in Table 2.

Comparative Examples 7 and 8

A drug sorption test was performed on the 24-well TCPS culture vessel (manufactured by Corning Incorporated, made of polystyrene (PS)) used in Comparative Example 4 and the 24-well PDMS culture vessel (product name: G-plate, VECELL (trademark) model number: V24WGPB-10) used in Comparative Example 5, taken as Comparative Examples 7 and 8, respectively. The results are shown in Table 2.

TABLE 2

|  | 4-methyl-1-pentene Polymer Vessel (Example 11) | PS Vessel (Comparative Example 7) | PDMS Vessel (Comparative Example 8) |
| --- | --- | --- | --- |
| Rhodamine B | 98% | 90% | 2% |
| Rhodamine 123 | 99% | 79% | 58% |
| Rhodamine 6G | 96% | 86% | 21% |
| Cyclosporin A | 58% | 56% | 2% |
| Ticlopidine Hydrochloride | 64% | 67% | 1% |
| Leflunomide | 68% | 70% | 2% |
| Troglitazone | 64% | 65% | 1% |
| Isoproterenol Hydrochloride | 63% | 65% | 1% |

Table 2 shows that, when the culture vessel in which the culture material of the present invention was placed at the bottom portion of the culture vessel was used (Example 11), the culture vessel was less likely to sorb the drugs, compared to the PS vessel and the PDMS vessel. That is, the culture material containing the 4-methyl-1-pentene polymer (X) of the present invention was superior in low drug sorption.

The results above revealed that, the culture material of the present invention is superior in shape stability and oxygen supply capacity as well as adhesion of cells, etc., and the culture material is superior in convenience since it emits no autofluorescence despite of being a resin vessel and thus enables cultured cells to be fluorescently observed as it is. Further, the culture material is low in drug sorption and therefore can be suitably used in applications of drug discovery screening and diagnosis.

INDUSTRIAL APPLICABILITY

The culture material of the present invention can culture a wide variety of cells as described above and can adapt to various culture methods according to cells and purposes. Further, the culture material of the present invention can be applied to still more applications when subjected to the hydrophilic treatment of the surface of the culture material and therefore has industrial applicability.

The invention claimed is:

1. A culture material comprising a 4-methyl-1-pentene polymer (X) for cells, tissues, or organs, the culture material having a water contact angle at a culture surface of 50° to 100°,
a sagging distance by a test method (A) described below of 0 to 5 mm, and
an oxygen permeation rate at a temperature of 23° C. and a humidity of 0% of 4500 to 90000 $cm^3/(m^2 \times 24\ h \times atm)$,
wherein the content of a structural unit derived from 4-methyl-1-pentene is 80 to 100 mol %, and the content of a structural unit derived from at least one type of olefin selected from ethylene and an α-olefin having 3 to 20 carbon atoms (excluding 4-methyl-1-pentene) is 0 to 20 mol %, with all repeating structural units being 100 mol %,
wherein the thickness of the culture material is 20 to 500 μm,
wherein the culture material is subjected to a hydrophilic treatment on its surface, and
wherein
in the test method (A), a test piece having the same material as the culture material and the same thickness as the culture surface of the culture material and having a flat plate shape of 100 mm long and 10 mm wide is made,
the test piece is fixed onto a test board in a state where the test piece protrudes lengthwise a length of 50 mm in a horizontal direction from a top surface of the test board, the top surface being horizontal, and
three minutes after fixing, a measurement is performed of a distance of how much an end of the test piece protruding from the test board sags in a vertically downward direction from a horizontal plane including the top surface of the test board, provided that the fixing to the measurement is performed at room temperature.

2. The culture material according to claim 1, wherein the 4-methyl-1-pentene polymer (X) is at least one type of polymer selected from a 4-methyl-1-pentene homopolymer (x1) and a copolymer (x2) of 4-methyl-1-pentene and at least one type of olefin selected from ethylene and an α-olefin having 3 to 20 carbon atoms (excluding 4-methyl-1-pentene).

3. The culture material according to claim 1, wherein when a test method (B) described below is performed with rat primary-cultured liver cells to be seeded having a cell density of $1.0 \times 10^5$ cells/$cm^2$ to $4.0 \times 10^5$ cells/$cm^2$, a dissolved oxygen concentration in a culture solution after 1 hour is 2 to 20% of a saturated oxygen concentration in the culture solution for at least one point in the range of the cell density,
in the test method (B), a culture vessel comprising a cylindrical portion composed of polyethylene and a bottom surface portion having a flat plate shape and having the same material as the culture material and the same thickness as the culture surface of the culture material, the culture vessel having a culture area of 2 $cm^2$ and being coated with collagen, is made, the culture vessel is seeded with rat primary-cultured liver cells with 0.5 ml of a culture solution for rat primary-cultured liver cells and cultured at a temperature of 37° C., a carbon dioxide concentration of 5.0%, and an oxygen concentration of 20%, twenty four hours after seeding, the culture solution is removed from the culture vessel, and 0.5 ml of the culture solution is newly added to the culture vessel, and an oxygen concentration is measured at 80 μm height from a bottom surface of the culture vessel for 1 hour.

4. The culture material according to claim 3, wherein when the test method (B) is performed with rat primary-cultured liver cells to be seeded having a cell density of $1.0 \times 10^5$ cells/$cm^2$ to $4.0 \times 10^5$ cells/$cm^2$, an oxygen consumption rate is 40 to 150 pmol/s/$10^5$ cells for at least one point in the range of the cell density.

5. The culture material according to claim 1, which is a film, a sheet, or a culture vessel.

6. The culture material according to claim 5, wherein the culture vessel is a petri dish, a flask, an insert, a plate, a bottle, or a bag.

7. The culture material according to claim 1, wherein the culture surface is microfabricated.

8. A microchannel device comprising the culture material according to claim 7.

9. A culture vessel, wherein at least a culture surface is formed of the culture material according to claim 1.

10. The culture vessel according to claim 9, comprising at least one well.

11. A culture tool comprising the culture material according to claim 1, wherein at least a culture surface is formed of the culture material.

12. The culture tool according to claim 11, wherein the culture surface is coated with a natural polymer material, a synthetic polymer material, or an inorganic material.

13. A method for culturing cells, tissues, or organs, comprising a step of incubating cells, tissues, or organs in the culture tool according to claim 11.

14. The method for culturing cells, tissues, or organs according to claim 13, wherein the cells, tissues, or organs are liver cells.

* * * * *